United States Patent
Singh

(10) Patent No.: US 9,375,408 B2
(45) Date of Patent: Jun. 28, 2016

(54) METHODS OF MAKING A DEUTERATED OR A NON-DEUTERATED MOLECULE AND PHARMACEUTICAL FORMULATIONS FOR TREATMENT

(71) Applicant: Bhupinder Singh, Phoenix, AZ (US)

(72) Inventor: Bhupinder Singh, Phoenix, AZ (US)

( * ) Notice: Subject to any disclaimer, the term of this patent is extended or adjusted under 35 U.S.C. 154(b) by 0 days.

(21) Appl. No.: 14/841,229

(22) Filed: Aug. 31, 2015

(65) Prior Publication Data

US 2016/0058713 A1  Mar. 3, 2016

Related U.S. Application Data

(60) Provisional application No. 62/044,566, filed on Sep. 2, 2014.

(51) Int. Cl.
| | |
|---|---|
| A61K 31/121 | (2006.01) |
| C07C 49/255 | (2006.01) |
| C07C 49/175 | (2006.01) |
| A61K 31/12 | (2006.01) |
| A61K 31/7048 | (2006.01) |
| A61K 31/381 | (2006.01) |
| A61K 31/355 | (2006.01) |
| A61K 31/375 | (2006.01) |
| A61K 31/16 | (2006.01) |
| A61K 31/145 | (2006.01) |
| A61K 31/01 | (2006.01) |

(52) U.S. Cl.
CPC ............... *A61K 31/12* (2013.01); *A61K 31/01* (2013.01); *A61K 31/145* (2013.01); *A61K 31/16* (2013.01); *A61K 31/355* (2013.01); *A61K 31/375* (2013.01); *A61K 31/381* (2013.01); *A61K 31/7048* (2013.01)

(58) Field of Classification Search
None
See application file for complete search history.

(56) References Cited

U.S. PATENT DOCUMENTS

| 6,503,921 B2 | 1/2003 | Naicker et al. |
| 8,575,221 B2 | 11/2013 | Masse et al. |
| 2014/0155961 A1 | 6/2014 | Morariu et al. |

FOREIGN PATENT DOCUMENTS

| JP | H11-246398 | * | 9/1999 | ............ A61K 31/12 |
| WO | WO2010/097643 | * | 9/2010 | ............ A61K 47/02 |
| WO | WO2011/047309 | * | 4/2011 | ............ A61K 31/12 |

OTHER PUBLICATIONS

Wu et al., "Chemopreventative effects of tetrahydrocurcumin on human diseases" Food and Function (2014) vol. 5 pp. 12-17.*
English macine translation of H11-246398 above, downloaded from EPO, published 1999.*
Nakmaerong et al., "Antioxidant and vascular protective effects of curcumin and tetrahydrocurcumin in rats with L-NAME-induced hypertension" Naunyn-Schmeid Arch Pharmacol (2011) vol. 383 pp. 519-529.*
Pan et al., "Experimental study of effects of tetrahydrocurcumin on fatty liver" Guangdong Yaoxueyuan Xuebao (2010) vol. 26 No. 6 pp. 617-623.*
Murugan et al., "Effect of Tetrahydrocurcumin on Lipid Peroxidation and Lipids in Streptozotocin-Nicotinamide-Induced Diabetic Rats" Basic and Clinical Pharmacology and Toxicology (2006) vol. 99 pp. 122-127.*
Goel, A., et al., "Curcumin as 'Curcumin': From kitchen to clinic," *Biochem. Pharmacol.* vol. 75, No. 4 Feb. 15, 2008, pp. 787-809.
Kawano, S., et al., Analysis of keto-enol tautomers of curcumin by liquid chromatography/mass spectrometry, *Chinese Chemical Letters*, vol. 24, 2013, pp. 685-687.
Setthacheewakul, S., et al., "Controlled Release of Oral Tetrahydrocurcumin from a Novel Self-Emulsifying Floating Drug Delivery System (SEFDDS)," *AAPS PharmSciTech*, vol. 12, No. 1, Mar. 2011, published online Dec. 23, 2010, pp. 152-164.
Osawa, T., "Nephroprotective and Hepatoprotective Effects of Curcuminoids," In: *The Molecular Targets and Therapeutic Uses of Curcumin in Health and Disease*, Advances in Experimental Medicine and Biology, vol. 595, 2007, pp. 407-423.
International Search Report and Written Opinion mailed Dec. 8, 2015 in PCT/US15/47822.

* cited by examiner

*Primary Examiner* — Eric Olson
(74) *Attorney, Agent, or Firm* — Knobbe, Martens, Olson & Bear, LLP

(57) ABSTRACT

Deuterated and non-deuterated forms of tetrahydrocurcumin are described herein. Methods of making tetrahydrocurcumin in deuterated and non-deuterated forms and pharmaceutical formulations including tetrahydrocurcumin in deuterated and non-deuterated forms are disclosed. Methods of treating a subject using deuterated forms of tetrahydrocurcumin or non-deuterated forms of tetrahydrocurcumin are also disclosed.

32 Claims, 8 Drawing Sheets

METHODS OF MAKING A DEUTERATED OR A NON-DEUTERATED MOLECULE AND PHARMACEUTICAL FORMULATIONS FOR TREATMENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57, for example, U.S. Provisional Patent Application No. 62/044,566, filed Sep. 2, 2014, which is hereby incorporated by reference in its entirety.

BACKGROUND

Many drugs can be administered through the oral route as liquids, capsules or tablets. As oral administration is a safe, convenient and cost effective route, it is the route taken for most therapeutics. However oral administration has several limitations. Orally administered drugs bypass the mouth and the stomach in order to be absorbed into the system for use. Drug absorption can begin in the mouth and stomach, and can be finally absorbed by the small intestine, passing the intestinal walls, passing through the liver for processing, and then finally be transported through the bloodstream to reach its target site. As such, the drugs can be metabolized before the blood and plasma are reached.

Drugs can be metabolized by oxidation, reduction, hydrolysis, conjugation, condensation and other additional processes that can make the drug easier for a subject to excrete. Some drugs can be metabolized so rapidly that a therapeutically effective concentration in the blood is not reached.

A property of orally administered drugs that can affect its ability to reach its destined tissue or site of treatment can be its absorption and solubility. Solubility behavior is a challenge for many drugs, which can require pharmaceutical formulations with solubility enhancers in order to improve its ability to become absorbed by a system for use. Solubility is a phenomenon of dissolution of solute into a solvent to give a homogenous system and is important for achieving a desired concentration of drug in a systemic circulation for a desired pharmacological response. The solubility of a drug is intrinsically related to its size and its properties. Low aqueous solubility is a problem for many drugs, as a drug will need to be in a form of a solution at the site of absorption, such as within the gastro-intestinal tract. To date, more than 40% of chemical entities developed for the pharmaceutical industry are poorly soluble in water. Solubility however can be increased by the drug solutions of oil in water emulsion, addition of a hydrophilic carrier, cellulosic derivatives, lipids, phospholipids and antioxidants. As such, methods are needed to increase the bioavailability of a drug, such as methods to slow the metabolism of a drug and increase solubility of a drug, in a subject in need is needed.

SUMMARY

In one aspect, a method of treating, inhibiting, or ameliorating a disorder in a subject is provided. The method includes, for example, administering a pharmaceutical formulation to the subject. The pharmaceutical formulation may include a non-deuterated form of tetrahydrocurcumin or a deuterated form of tetrahydrocurcumin and a pharmaceutical vehicle. In some embodiments, the disorder is selected from a group including fatty liver disease, alcoholic liver disease, kidney disease, diabetic kidney disease, polycystic kidney disease, hypertension, hypertension with left ventricular hypertrophy, heart failure, diabetes and diabetes with hyperlipidemia. In some embodiments, the subject has elevated levels of Galectin-3, fibrotic markers, markers of oxidative stress, and/or markers of inflammation in the blood and/or urine. In some embodiments, the subject is taking analgesics. In some embodiments, the subject is under treatment with one or more anti-malarial drugs. In some embodiments, the pharmaceutical formulation is administered by oral administration or intravenous administration.

In another aspect, a method of protecting an organ is provided. The method includes, for example, identifying a subject in need of protection of an organ and administering a pharmaceutical formulation to a subject in need thereof, the pharmaceutical formulation including a non-deuterated form of tetrahydrocurcumin or a deuterated form of tetrahydrocurcumin and a pharmaceutical vehicle. In some embodiments, the organ is selected from a group including kidney, liver and heart. In some embodiments, the administering is performed by oral administration or intravenous administration. In some embodiments, the subject has a disorder selected from a group including liver disorder, fatty liver disease, alcoholic liver disease, kidney disease, diabetic kidney disease, polycystic kidney disease, hypertension, hypertension with left ventricular hypertrophy, diabetes, diabetes with hyperlipidemia and heart failure. In some embodiments, the subject has an elevated level of Galectin-3, fibrotic markers, markers of oxidative stress and/or one or more markers of inflammation in the blood and/or urine.

In another aspect a method of treating or preventing heart failure in a subject in need thereof is provided. The method includes, for example, identifying a subject in need of treatment for or prevention of heart failure and administering pharmaceutical formulation to a subject in need thereof, the pharmaceutical formulation including a non-deuterated form of tetrahydrocurcumin or a deuterated form of tetrahydrocurcumin and a pharmaceutical vehicle. In some embodiments, the subject has chronic kidney disease and/or hypertension. In some embodiments, the administering is oral administration or intravenous administration.

In another aspect a pharmaceutical formulation includes a non-deuterated form of tetrahydrocurcumin or a deuterated form of tetrahydrocurcumin and a pharmaceutical vehicle is provided. In some embodiments, the pharmaceutical formulation includes, for example, a first lipid. In some embodiments, the first lipid is a phospholipid or polyenylphosphatidylcholine. In some embodiments, the pharmaceutical formulation includes at least 5% of the first lipid by weight and no more than 95% of the first lipid by weight. In some embodiments, the pharmaceutical formulation further includes a second lipid. In some embodiments, the pharmaceutical formulation includes at least 5% of the second lipid by weight and no more than 95% of the second lipid by weight. In some embodiments, the pharmaceutical formulation further includes an antioxidant. In some embodiments, the pharmaceutical formulation includes at least 5% of antioxidant by weight and no more than 95% of the antioxidant by weight. In some embodiments, the antioxidant is selected from a group consisting of Vitamin E, Vitamin C and alpha lipoic acid. In some embodiments, the pharmaceutical formulation further includes curcumin, a terpenoid, cysteamine, pantethine, and/or baicalin. In some embodiments, the vehicle is a lipophilic solvent, fatty oil, organic oil, or liposome. In some embodiments, the pharmaceutical formulation further includes an excipient. In some embodiments, the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

In a first aspect, a method treating, inhibiting, or ameliorating a disorder in a subject is provided. In some embodiments, the method includes administering the pharmaceutical formulation including a non-deuterated form of tetrahydrocurcumin of any of the embodiments described herein. In some embodiments, the disorder is a liver disorder. In some embodiments, the disorder is a fatty liver disease. In some embodiments, the disorder is alcoholic liver disease. In some embodiments, the disorder is a kidney disease. In some embodiments, the disorder is diabetic kidney disease. In some embodiments, the disorder is polycystic kidney disease. In some embodiments, the disorder is hypertension. In some embodiments, the disorder is hypertension with left ventricular hypertrophy. In some embodiments, the disorder is diabetes. In some embodiments, the disorder is diabetes with hyperlipidemia. In some embodiments, the subject has elevated Galectin-3 levels in the blood and/or urine. In some embodiments, the subject has elevated levels of fibrotic markers. In some embodiments, the fibrotic markers are in blood. In some embodiments, the fibrotic markers are in urine. In some embodiments, the subject has an elevated level of a marker of oxidative stress. In some embodiments, the marker of oxidative stress is in blood. In some embodiments, the marker of oxidative stress is in urine. In some embodiments, the subject has an elevated level of a marker of inflammation. In some embodiments, the marker of inflammation is in blood. In some embodiments, the marker of inflammation is in urine. In some embodiments, the pharmaceutical formulation is administered to the subject by oral administration. In some embodiments, the administering is performed by intravenous administration. In some embodiments, the subject is human. In some embodiments, the subject is taking analgesics. In some embodiments, the subject is under treatment with one or more anti-malarial drugs. In some embodiments, the subject has heart failure.

In a second aspect, a method of protecting an organ is provided. In some embodiments, the method includes identifying a subject in need of protection of an organ; and administering the pharmaceutical formulation including a non-deuterated form of tetrahydrocurcumin of any of the embodiments described herein to a subject in need. In some embodiments, the method includes identifying a subject in need of protection of an organ and administering the pharmaceutical formulation including a non-deuterated form of tetrahydrocurcumin according to any of the embodiments described herein to the subject in need. In some embodiments, the organ is kidney. In some embodiments, the organ is liver. In some embodiments, the subject is human. In some embodiments, the organ is heart.

In some embodiments, the administering is performed by oral administration. In some embodiments, the administering is performed by intravenous administration. In some embodiments, the subject has a liver disorder. In some embodiments, the subject has a fatty liver disease. In some embodiments, the subject has alcoholic liver disease. In some embodiments, the subject has a kidney disease. In some embodiments, the subject has diabetic kidney disease. In some embodiments, the subject has polycystic kidney disease. In some embodiments, the subject has heart failure.

In some embodiments, the subject has hypertension. In some embodiments, the subject has hypertension with left ventricular hypertrophy. In some embodiments, the subject has diabetes. In some embodiments, the subject has diabetes with hyperlipidemia.

In some embodiments, the subject has an elevated level of Galectin-3 in the blood. In some embodiments, the subject has an elevated level of one or more fibrotic markers. In some embodiments, the one or more fibrotic markers are in blood. In some embodiments, at least one of the one or more fibrotic markers is in urine. In some embodiments, the subject has an elevated level of one or more markers of oxidative stress. In some embodiments, at least one of the markers of oxidative stress is in blood. In some embodiments, at least one of the markers of oxidative stress is in urine. In some embodiments, the subject has an elevated level of one or more markers of inflammation. In some embodiments, at least one of the elevated markers of inflammation is in blood. In some embodiments, at least one of the elevated markers is in urine.

In a third aspect, a method of treatment or preventing heart failure in a subject in need is provided. The method can include identifying a subject in need of treatment for or prevention of heart failure and administering the pharmaceutical formulation including a non-deuterated form of tetrahydrocurcumin of any one of the embodiments described herein to a subject in need. In some embodiments, the subject has chronic kidney disease and/or hypertension. In some embodiments, the subject is human. In some embodiments, the administering is performed by oral administration. In some embodiments, the administering is performed by intravenous administration.

In a fourth aspect, a pharmaceutical formulation is provided. In some embodiments, the pharmaceutical formulation includes a non-deuterated form of tetrahydrocurcumin and a pharmaceutical vehicle. In some embodiments, the pharmaceutical formulation includes a first lipid. In some embodiments, the first lipid is a phospholipid. In some embodiments, the first lipid is polyenylphosphatidylcholine. In some embodiments, the pharmaceutical formulation includes at least 5% of the first lipid by weight. In some embodiments, the pharmaceutical formulation includes no more than 95% of the first lipid by weight. In some embodiments, the pharmaceutical formulation further includes a second lipid. In some embodiments, the pharmaceutical formulation includes at least 5% of the second lipid by weight. In some embodiments, the pharmaceutical formulation includes no more than 95% of the second lipid by weight. In some embodiments, the second lipid is omega-3. In some embodiments, the second lipid is omega-3 from fish or flaxseed. In some embodiments, the pharmaceutical formulation includes an antioxidant. In some embodiments, the pharmaceutical formulation includes at least 5% of antioxidant by weight. In some embodiments, the pharmaceutical formulation includes no more than 95% of the antioxidant by weight. In some embodiments, the antioxidant is Vitamin E. In some embodiments, the antioxidant is Vitamin C. In some embodiments, the antioxidant is alpha lipoic acid. In some embodiments, the pharmaceutical formulation further includes curcumin. In some embodiments, the pharmaceutical formulation further includes a terpenoid. In some embodiments, the pharmaceutical formulation further includes cysteamine. In some embodiments, the pharmaceutical formulation further includes pantethine. In some embodiments, the curcumin is deuterated. In some embodiments, the vehicle is a lipophilic solvent, fatty oil, organic oil, or liposome. In some embodiments, the pharmaceutical formulation further includes an excipient. In some embodiments, the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In some embodiments, the pharmaceutical formulation further includes baicalin.

In a fifth aspect, a non-deuterated form of tetrahydrocurcumin is provided.

In a sixth aspect, a deuterated form of tetrahydrocurcumin is provided. In some embodiments, the deuterated form of tetrahydrocurcumin has no more than fifteen deuterated sites. In some embodiments, the deuterated form of tetrahydrocurcumin has at least ten deuterated sites. In some embodiments, the deuterated form of tetrahydrocurcumin has at least five deuterated sites. In some embodiments, the deuterated form of tetrahydrocurcumin has at least one deuterated site. In some embodiments, the deuterated form of tetrahydrocurcumin is deuterated at one or two alcohol sites. In some embodiments, the deuterated form of tetrahydrocurcumin has at least 1 deuteron. In some embodiments, the deuterated form of tetrahydrocurcumin has at least 5 deuterons. In some embodiments, the deuterated form of tetrahydrocurcumin has at least 10 deuterons. In some embodiments, the deuterated form of tetrahydrocurcumin has at least 20 deuterons. In some embodiments, the deuterated form of tetrahydrocurcumin has at least 24 deuterons.

In a seventh aspect, a method of making a deuterated form of tetrahydrocurcumin is provided. In some embodiments, the method includes contacting tetrahydrocurcumin in the presence of a catalyst and deuterated water under a condition to form the deuterated form of tetrahydrocurcumin. In some embodiments, the method further includes hydrogenating curcumin to form the tetrahydrocurcumin. In some embodiments, the deuterated form of tetrahydrocurcumin has at least one deuterated site. In some embodiments, the deuterated form of tetrahydrocurcumin has at least five deuterated sites. In some embodiments, the deuterated form of tetrahydrocurcumin has at least ten deuterated sites. In some embodiments, the deuterated form of tetrahydrocurcumin has no more than fifteen deuterated sites. In some embodiments, the deuterated form of tetrahydrocurcumin is deuterated at one or two alcohol sites. In some embodiments, the deuterated form of tetrahydrocurcumin has no more than twenty-four deuterons. In some embodiments, the deuterated form of tetrahydrocurcumin has at least 1 deuteron. In some embodiments, the deuterated form of tetrahydrocurcumin has at least 5 deuterons. In some embodiments, the deuterated form of tetrahydrocurcumin has at least 10 deuterons. In some embodiments, the deuterated form of tetrahydrocurcumin has at least 20 deuterons. In some embodiments, the deuterated form of tetrahydrocurcumin has at least 24 deuterons.

In some embodiments, the catalyst is palladium on carbon. In some embodiments, the catalyst is palladium barium carbonate. In some embodiments, the catalyst is palladium barium sulphate. In some embodiments, the catalyst is palladium silica. In some embodiments, the catalyst is platinum on carbon. In some embodiments, the catalyst is platinum-palladium carbon. In some embodiments, the catalyst is platinum alumina. In some embodiments, the catalyst is platinum calcium carbonate. In some embodiments, the catalyst is platinum barium sulfate. In some embodiments, the catalyst is platinum silica. In some embodiments, the catalyst is platinum graphite.

In some embodiments, the method further includes purifying the deuterated form of tetrahydrocurcumin. In some embodiments, the purifying step includes isolating the deuterated form of tetrahydrocurcumin with column chromatography. In some embodiments, the deuterated water is at least 25% deuterated. In some embodiments, the deuterated water is at least 50% deuterated. In some embodiments, the deuterated water is at least 75% deuterated. In some embodiments, the deuterated water is 100% deuterated.

In an eighth aspect, a pharmaceutical formulation, for example a pharmaceutical formulation, including a deuterated form of tetrahydrocurcumin is provided. In some embodiments, the pharmaceutical formulation includes a deuterated form of tetrahydrocurcumin and a pharmaceutical vehicle. In some embodiments, the deuterated form of tetrahydrocurcumin has no more than fifteen deuterated sites. In some embodiments, the deuterated form of tetrahydrocurcumin has at least ten deuterated sites. In some embodiments, the deuterated form of tetrahydrocurcumin has at least five deuterated sites. In some embodiments, the deuterated form of tetrahydrocurcumin has at least one deuterated site. In some embodiments, the deuterated form of tetrahydrocurcumin is deuterated at one or two alcohol sites. In some embodiments, the deuterated form of tetrahydrocurcumin has at least 1 deuteron. In some embodiments, the deuterated form of tetrahydrocurcumin has at least 5 deuterons. In some embodiments, the deuterated form of tetrahydrocurcumin has at least 10 deuterons. In some embodiments, the deuterated form of tetrahydrocurcumin has at least 20 deuterons. In some embodiments, the deuterated form of tetrahydrocurcumin has at least 24 deuterons.

In some embodiments, the pharmaceutical formulation further includes a first lipid. In some embodiments, the first lipid is a phospholipid. In some embodiments, the first lipid is polyenylphosphatidylcholine. In some embodiments, the pharmaceutical formulation includes at least 5% of the first lipid by weight. In some embodiments, the pharmaceutical formulation includes no more than 95% of the first lipid by weight. In some embodiments, the pharmaceutical formulation includes a second lipid. In some embodiments, the pharmaceutical formulation includes at least 5% of the second lipid by weight. In some embodiments, the pharmaceutical formulation includes no more than 95% of the second lipid by weight. In some embodiments, the second lipid is omega-3. In some embodiments, the second lipid is omega-3 from fish or flaxseed.

In some embodiments, the pharmaceutical formulation includes an antioxidant. In some embodiments, the pharmaceutical formulation includes at least 5% of antioxidant by weight. In some embodiments, the pharmaceutical formulation includes no more than 95% of the antioxidant by weight. In some embodiments, the antioxidant is Vitamin E. In some embodiments, the antioxidant is Vitamin C. In some embodiments, the antioxidant is alpha lipoic acid.

In some embodiments, the pharmaceutical formulation further includes curcumin. In some embodiments, the curcumin is deuterated. In some embodiments, the pharmaceutical formulation includes a terpenoid. In some embodiments, the pharmaceutical formulation includes cysteamine. In some embodiments, the pharmaceutical formulation includes pantethine. In some embodiments, the pharmaceutical formulation includes baicalin. In some embodiments, the vehicle is a lipophilic solvent, fatty oil, organic oil, or liposome. In some embodiments, the pharmaceutical formulation further includes an excipient. In some embodiments, the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

In a ninth aspect, a method of treating, inhibiting, or ameliorating a disorder in a subject is provided. In some embodiments, the method includes administering a pharmaceutical formulation includes a deuterated form of tetrahydrocurcumin according to any of the embodiments described herein to the subject. In some embodiments, the disorder is a liver disorder. In some embodiments, the disorder is a fatty liver disease. In some embodiments, the disorder is alcoholic liver disease. In some embodiments, the disorder is a kidney disease. In some embodiments, the disorder is diabetic kidney disease. In some embodiments, the disorder is polycystic kidney disease.

In some embodiments, the disorder is hypertension. In some embodiments, the disorder is hypertension with left ventricular hypertrophy. In some embodiments, the disorder is diabetes. In some embodiments, the disorder is diabetes with hyperlipidemia. In some embodiments, the disorder is heart failure.

In some embodiments, the subject has elevated Galectin-3 levels in the blood. In some embodiments, the subject has elevated levels of fibrotic markers. In some embodiments, the fibrotic markers are in blood. In some embodiments, the fibrotic markers are in urine. In some embodiments, the subject has an elevated level of a marker of oxidative stress. In some embodiments, the marker of oxidative stress is in blood. In some embodiments, the marker of oxidative stress is in urine. In some embodiments, the subject has an elevated level of a marker of inflammation. In some embodiments, the marker of inflammation is in blood. In some embodiments, the marker of inflammation is in urine.

In some embodiments, the pharmaceutical formulation is administered to the subject by oral administration. In some embodiments, the administering is performed by intravenous administration. In some embodiments, the subject is human. In some embodiments, the administering is performed by intravenous administration. In some embodiments, the subject is under treatment with one or more anti-malarial drugs.

In a tenth aspect a method of protecting an organ is provided. In some embodiments, the method includes identifying a subject in need of protection of an organ and administering the pharmaceutical formulation including a deuterated form of tetrahydrocurcumin according to any of the embodiments described herein to the subject in need. In some embodiments, the organ is kidney. In some embodiments, the organ is liver. In some embodiments, the organ is heart. In some embodiments, the subject is human.

In some embodiments, the administering is performed by oral administration. In some embodiments, the administering is performed by intravenous administration. In some embodiments, the subject has a liver disorder. In some embodiments, the subject has a fatty liver disease. In some embodiments, the subject has alcoholic liver disease. In some embodiments, the subject has a kidney disease. In some embodiments, the subject has diabetic kidney disease. In some embodiments, the subject has polycystic kidney disease. In some embodiments, the subject has heart failure.

In some embodiments, the subject has hypertension. In some embodiments, the subject has hypertension with left ventricular hypertrophy. In some embodiments, the subject has diabetes. In some embodiments, the subject has diabetes with hyperlipidemia.

In some embodiments, the subject has an elevated level of Galectin-3 in the blood. In some embodiments, the subject has an elevated level of one or more fibrotic markers. In some embodiments, the one or more fibrotic markers are in blood. In some embodiments, at least one of the one or more fibrotic markers is in urine. In some embodiments, the subject has an elevated level of one or more markers of oxidative stress. In some embodiments, at least one of the markers of oxidative stress is in blood. In some embodiments, at least one of the markers of oxidative stress is in urine. In some embodiments, the subject has an elevated level of one or more markers of inflammation. In some embodiments, at least one of the elevated markers of inflammation is in blood. In some embodiments, at least one of the elevated markers is in urine.

In an eleventh aspect, a method of treating or treating or preventing heart failure in a subject in need is provided. In some embodiments, the method includes identifying a subject in need of treatment for or prevention of heart failure administering the pharmaceutical formulation including a deuterated form of tetrahydrocurcumin of any one of any one of the embodiments described herein to a subject in need. In some embodiments, the subject has chronic kidney disease and/or hypertension. In some embodiments, the subject is human. In some embodiments, the administering is performed by oral administration. In some embodiments, the administering is performed by intravenous administration.

BRIEF DESCRIPTION OF THE DRAWINGS

FIG. 2A shows the average blood urea nitrogen (BUN) in the four groups of rats. FIG. 2B shows the change in BUN, or delta-BUN. FIG. 2C shows the Body Weight in the four groups of rats FIG. 2D shows the amount of Hemoglobin (Hgb) in the four groups of rats. FIG. 2E shows the Heart wt to Body wt (g/kg) ratio of the four groups of rats. FIG. 2F shows the systolic blood pressure in the four groups of rats. FIG. 2G shows the diastolic blood pressure in the four groups of rats.

DETAILED DESCRIPTION

Figure 1:
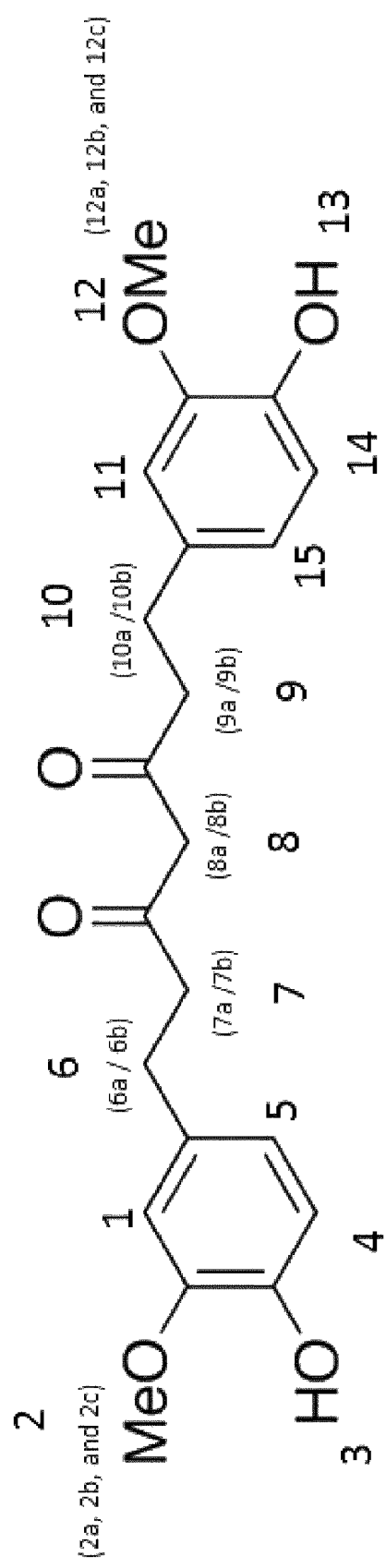
FIG. 1 shows a schematic illustration of tetrahydrocurcumin. Sites are numbered on the schematic illustration of tetrahydrocurcumin to indicate non-limiting exemplary deuteration sites. In one or more of these deuteration sites, there can be one, two, or three deuterons.
Figure 2A:
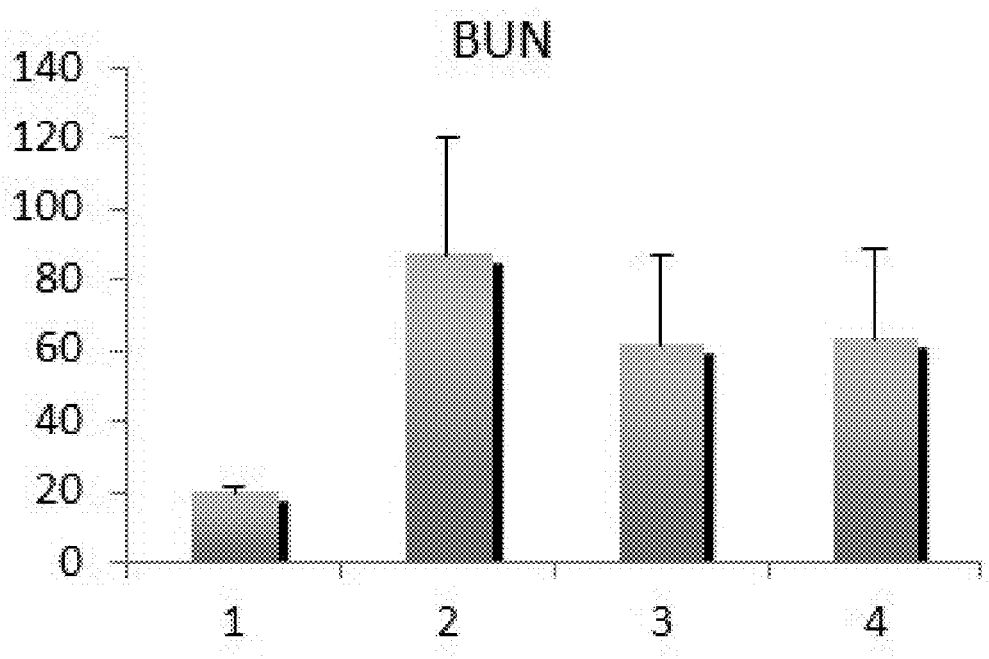
FIGS. 2A-2G show the measurements between the four groups of rats: 1) control rats 2) rats with chronic kidney disease (CKD), 3) rats treated with tetrahydrocurcumin after CDK, and 4) rats treated with tetrahydrocurcumin/curcumin after CDK.
Figure 2B:
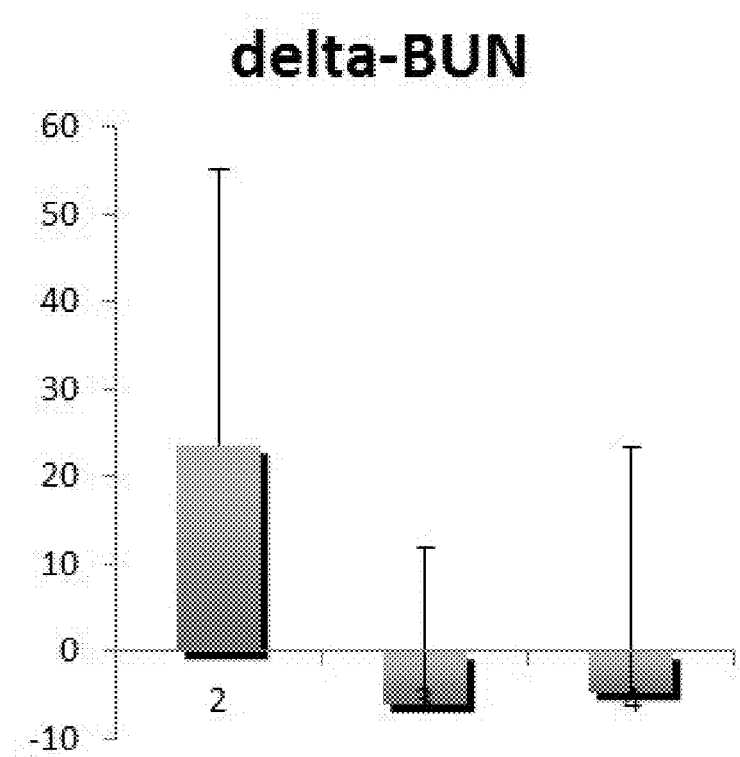
Figure 2C:
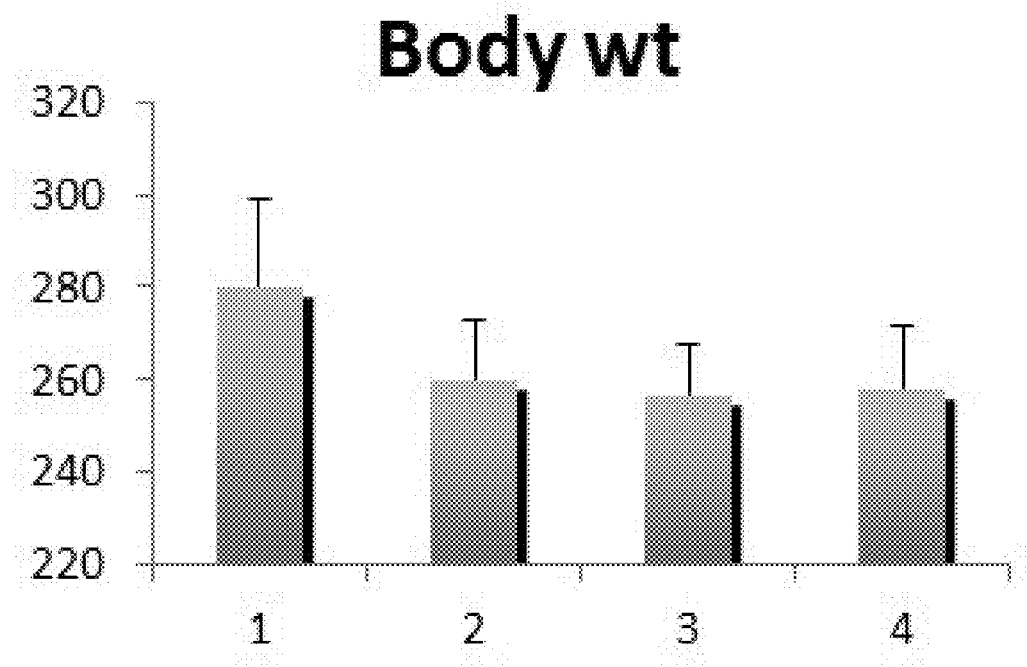
Figure 2D:
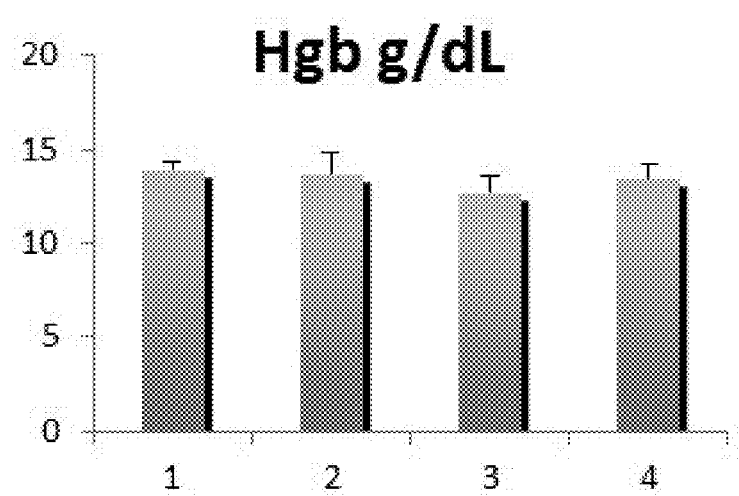
Figure 2E:
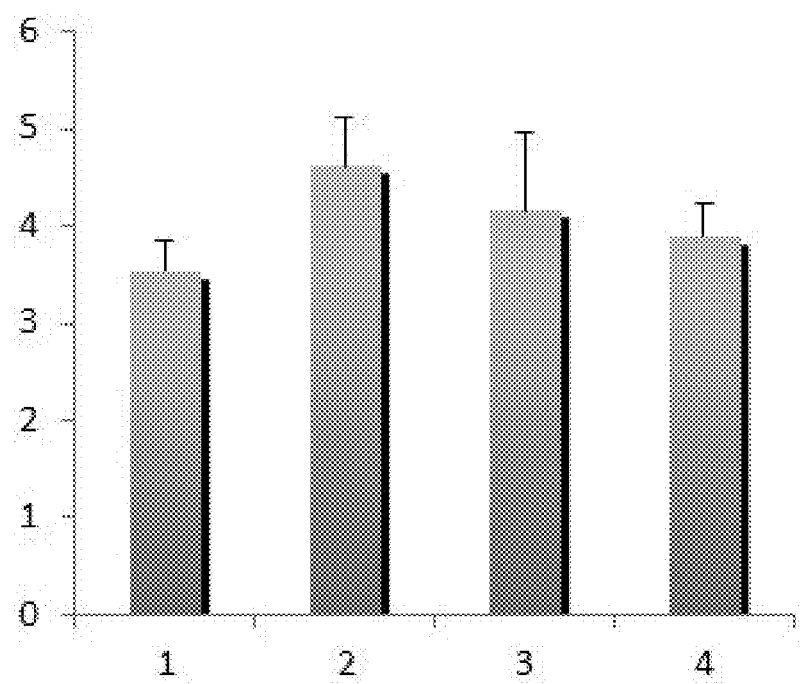
Figure 2F:
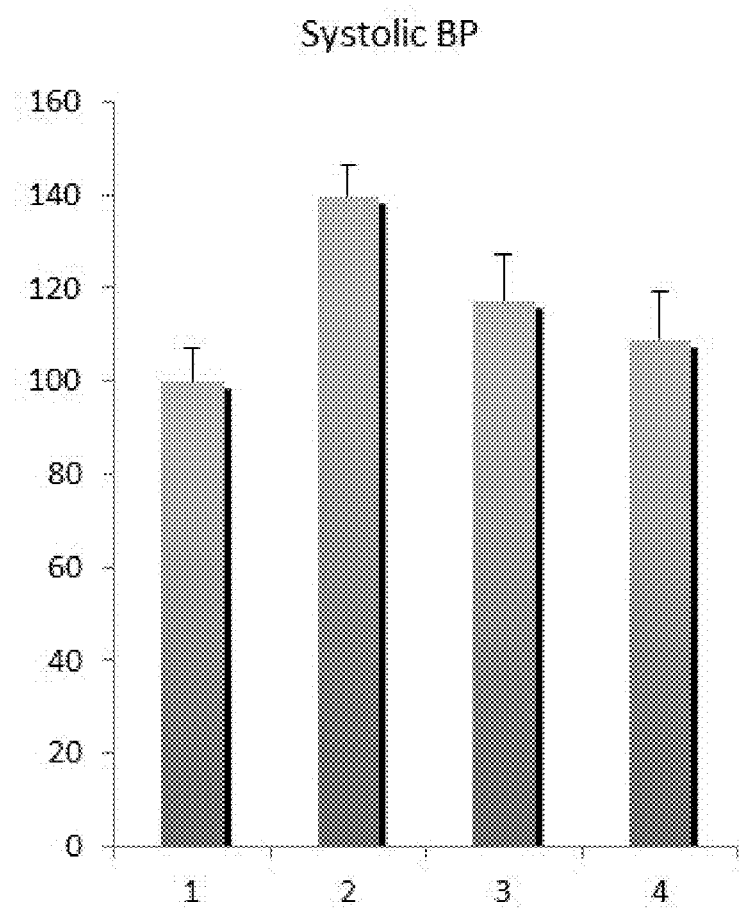
Figure 2G:
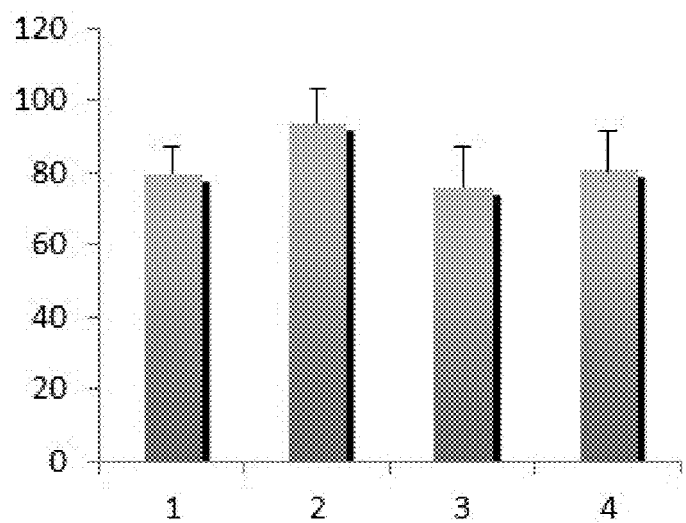

Many drugs can be administered through the oral route as liquids, capsules or tablets. As oral administration is a safe, convenient and cost effective route, it is the route taken for most therapeutics. However oral administration has several limitations. Orally administered drugs bypass the mouth and the stomach in order to be absorbed into the system for use. Drug absorption can begin in the mouth and stomach, and can be finally absorbed by the small intestine, passing the intestinal walls, passing through the liver for processing, and then finally be transported through the bloodstream to reach its target site. As such, the drugs can be metabolized before the blood and plasma are reached.

"Bioavailability" as described herein, refers to the absorption of a drug or drugs and is a subcategory of absorption as is the fraction of an administered dose of unchanged drug that reaches the systemic circulation and is one of the principal pharmacokinetic properties of drugs. Bioavailability thereby can refer to the extent and rate at which the active drug or metabolite enters the systemic circulation to reach the site for action. Low bioavailability is the most common problem of orally administered drugs, as many are poorly water soluble and slowly absorbed drugs. The bioavailability of a drug is affected by the function of the intestinal walls and the liver, in which enzymatic reactions can metabolize the drug, thus decreasing the amount of the drug that eventually reaches the blood stream for delivery. This in effect decreases the bioavailability of a drug, or its extent and rate at which the active drug enters the systemic circulation.

Drugs can be metabolized by oxidation, reduction, hydrolysis, conjugation, condensation and other additional processes that can make the drug easier for a subject to excrete. Some drugs can be metabolized so rapidly that a therapeutically effective concentration in the blood is not reached.

A property of orally administered drugs that can affect its ability to reach its destined tissue or site of treatment can be its absorption and solubility. Solubility behavior is a challenge for many drugs, which can require pharmaceutical formulations with solubility enhancers in order to improve its ability to become absorbed by a system for use. Solubility is a phenomenon of dissolution of solute into a solvent to give a homogenous system and is important for achieving a desired concentration of drug in a systemic circulation for a desired pharmacological response. The solubility of a drug is intrinsically related to its size and its properties. Low aqueous solubility is a problem for many drugs, as a drug will need to be in a form of a solution at the site of absorption, such as within the gastro-intestinal tract. To date, more than 40% of chemical entities developed for the pharmaceutical industry are poorly soluble in water. Solubility however can be increased by the drug solutions of oil in water emulsion, addition of a hydrophilic carrier, cellulosic derivatives, lipids, phospholipids and antioxidants. In some embodiments, a pharmaceutical formulation is provided. In some embodiments, the pharmaceutical formulation is administered to a subject by oral administration. In some embodiments, the subject is human. In some embodiments, the administering is performed by intravenous administration.

Drug solutions of oil and surfactants can form oil in water emulsions upon mixing with aqueous media in the gastro-intestinal tract, which can lead to an increase in drug absorption of a drug with poor solubility. Pharmaceutical formulations comprising lipids can also be used to increase the bioavailability of a drug by increasing its absorption. Lipids, as described herein refers to fatty acids, or fatty acid residues that are hydrophobic or amphiphilic small molecules that can form structures, liposomes, or membranes when exposed to an aqueous environment such as liquids in a gastro-intestinal tract. Lipids can be categorized into fatty acids, glycerolipids, glycerophospholipids, phospholipids, sphingolipids, sterol lipids, prenol lipids, saccharolipids, and polyketides. In some embodiments, a pharmaceutical formulation comprising one or more lipids is provided. In some embodiments, the pharmaceutical formulation comprises a lipid. In some embodiments, the pharmaceutical formulation comprises a phospholipid.

Examples of phospholipids include, but are not limited to, phosphatidic acid, phosphatidylethanolamine, phosphatidylcholine, phosphatidylserine, phosphatidylinositol, phosphatidylinositol phosphate, phosphatidylinositol bisphosphate, phosphatidylinositol triphosphate, ceramide phosphorylcholine, ceramide phosphorylethanolamine, ceramide phosphorylipid, phosphatidylcholine and polyenylphosphatidylcholine. Polyenylphosphatidyl choline can have the added benefit of increasing the bioavailability by allowing absorption of a drug in the gut; additionally polyenylphosphatidyl choline has added benefits to hepatic health. For example, polyenylphosphatidyl choline has been shown to reduce free phenol and ammonia concentrations in subjects suffering from liver cirrhosis, this indicating that oxidative processes were ameliorated and detoxification processing in the liver was improved. In some embodiments, the pharmaceutical formulation disclosed herein comprises a non-deuterated form of tetrahydrocurcumin. In some embodiments, the pharmaceutical formulation comprises deuterated forms of tetrahydrocurcumin, as described in several embodiments herein. In some embodiments, the pharmaceutical formulation disclosed herein comprises a non-deuterated form of tetrahydrocurcumin and a deuterated form of tetrahydrocurcumin, as described in several embodiments herein. In some embodiments, pharmaceutical formulations disclosed herein comprise a lipid. In some embodiments, pharmaceutical formulations disclosed herein comprise a phospholipid. In some embodiments, pharmaceutical formulations disclosed herein comprise polyenylphosphatidylcholine. In some embodiments, pharmaceutical formulations disclosed herein comprise a phosphatidylcholine. The pharmaceutical formulation disclosed herein can comprise a first lipid. The first lipid can be any of the lipids disclose herein or a mixture thereof. In some embodiments, the pharmaceutical formulation comprises at least 5% of the first lipid by weight. In some embodiments, the pharmaceutical formulation comprises no more than 95% of the first lipid by weight. In some embodiments, the pharmaceutical formulation comprises a second lipid. In some embodiments, the pharmaceutical formulation comprises at least 5% of the second lipid by weight. In some embodiments, the pharmaceutical formulation comprises no more than 95% of the second lipid by weight. In some embodiments, the second lipid is omega-3. The second lipid can be any of the lipids disclose herein or a mixture thereof.

Pharmaceutical formulations comprising drugs or molecules of interest can also comprise elements that can have beneficial effects on organs that are being treated. For example lipids and anti-oxidants can be used, which can have beneficial effects for preventing or treating oxidative stress, fibrosis and scarring. Examples of lipids that can be included in the pharmaceutical formulations disclosed herein can include, but are not limited to, oils, emulsions, and omega-3 from fish oil, omega-3 from flaxseed, and omega-3 from walnuts. In some embodiments, the pharmaceutical formulation disclosed herein comprises a non-deuterated form of tetrahydrocurcumin. In some embodiments, the pharmaceutical formulation comprises deuterated forms of tetrahydrocurcumin, as described in several embodiments herein. In some embodiments, the pharmaceutical formulation disclosed herein comprises a non-deuterated form of tetrahydrocurcumin and a deuterated form of tetrahydrocurcumin, as described in several embodiments herein. In some embodiments, pharmaceutical formulations are provided comprising lipids. In some embodiments, the lipids are phospholipids. In some embodiments, the lipids are omega-3. In some embodiments, the lipids are polyenylphosphatidylcholine.

Anti-oxidants, as described herein refers to a molecule that can inhibit the oxidation of molecules and can include but is not limited to glutathione, vitamin C, vitamin A, vitamin E and alpha lipoic acid. Vitamin E acts as a peroxyl radical scavenger, and can prevent the propagation of free radicals in tissues by reacting with free radicals to form a tocopheryl radical, which can then be reduced by a hydrogen donor to return to its reduced state. Additionally, vitamin E is fat soluble and can incorporate itself into cell membranes to protect the membrane lipids from oxidative damage. Vitamin C, or ascorbic acid, is a co-factor in several enzymatic reactions, and also acts as a reducing agent, reversing oxidation in liquids, and plays a role in oxidative stress. Lipoic acid, or α-lipoic acid is an antioxidant and a co-factor for several enzymes. By adding lipids and antioxidants to drug pharmaceutical formulations, synergistic activities of the lipids and antioxidant with a drug can benefit the treatment of an organ.

In some embodiments, the pharmaceutical formulation disclosed herein comprises a non-deuterated form of tetrahydrocurcumin. In some embodiments, the pharmaceutical formulation comprises deuterated forms of tetrahydrocurcumin, as described in several embodiments herein. In some embodiments, the pharmaceutical formulation disclosed herein comprises a non-deuterated form of tetrahydrocurcumin and a deuterated form of tetrahydrocurcumin, as described in several embodiments herein. In some embodiments, pharmaceutical formulations are provided comprising lipids. In some embodiments, the lipids are phospholipids. In some embodiments, the lipids are omega-3. In some embodiments, the lipids are polyenylphosphatidylcholine. In some embodiments, a pharmaceutical formulation is provided comprising an antioxidant. In some embodiments, the antioxidant is Vitamin E. In some embodiments, the antioxidant is vitamin C. In some embodiments, the antioxidant is alpha lipoic acid. The pharmaceutical formulations disclosed herein can comprise one or more antioxidants. In some embodiments, the pharmaceutical formulation comprises at least 5% of antioxidant by weight. In some embodiments, the pharmaceutical formulation comprises no more than 95% of the antioxidant by weight. In some embodiments, the pharmaceutical formulation comprises about 5%, 10%, 15%, 20%, 30%, 35%, 40%, 45%, 50%, 55%, 60%, 65%, 70%, 75%, 80%, 85%, 90% 95% or any other value between these values of the antioxidant by weight.

A "dietary supplement" as described herein, refers to nutrients for growth and health. Without being limiting, examples of dietary supplements can include but are not limited to baicalin, cysteamine, vitamins, curcumin, terpenoids, and pantethine. "Cysteamine" as used herein, can refer to a chemical compound that is a stable aminothiol and degradation metabolite of the amino acid cysteine. Cysteamine is a cystine depleting agent and works by reducing the amount of cysteine in a body. "Pantethine," as used herein, can refer to a dietary supplement that is a dimeric form of vitamin B5. Pantethine can be used to improve a blood cholesterol profile. "Vitamins," as used herein, refers to a vital nutrient that an organism requires in small amounts for normal growth and development. When the organism cannot synthesize the nutrient in sufficient quantities, a vitamin is needed. Without being limiting, examples of vitamins can include vitamin A, vitamin B1, vitamin B2, vitamin B3, vitamin B5, vitamin B6, vitamin B7, vitamin B9, vitamin B12, vitamin C, vitamin D, vitamin E, and vitamin K. "Baicalin," as described herein refers to a flavonoid that is found in several species of plants from the genus *Scutellaria*. Baicalin is a known prolyl endopeptidase inhibitor, a potential anti-inflammatory drug, antibacterial, a hepatoprotective drug, and has been shown to exhibit multiple activities against severe acute pancreatitis, pancreatic cancer, obesity, metabolic disorders, and cancer.

"Terpenoids" as described herein, are a large diverse class of naturally occurring organic chemicals that are derived from five carbon isoprene units assembled and modified in multiple ways. Terpenoids are a subclass of prenyllipids. They can have their methyl groups moved or removed and oxygen atoms can be added. Terpenoids are the largest group of natural compounds and are known to those skilled in the art of their biological activities and their use in treatment of disease. Many are multicyclic that can differ in functional groups and in their basic carbon skeletons. Several examples include but are not limited to hemiterpenoids, monoterpenoids, sesquitepenoids, diterpenoids, sesterterpenoids, triterpenoids, tetraterpenoids, and polyterpenoid.

In some embodiments, the pharmaceutical formulations can comprise a dietary supplement. In some embodiments, the pharmaceutical formulation comprises cysteamine. In some embodiments, the pharmaceutical formulation comprises pantethine. In some embodiments, the pharmaceutical formulation comprises baicalin. In some embodiments, the pharmaceutical formulation comprises curcumin. In some embodiments, the pharmaceutical formulation disclosed herein comprises a non-deuterated form of tetrahydrocurcumin. In some embodiments, the pharmaceutical formulation comprises deuterated forms of tetrahydrocurcumin, as described in several embodiments herein. In some embodiments, the pharmaceutical formulation disclosed herein comprises a non-deuterated form of tetrahydrocurcumin and a deuterated form of tetrahydrocurcumin, as described in several embodiments herein.

In some embodiments, the pharmaceutical formulations disclosed herein can comprise one or more terpenoids. In some embodiments the pharmaceutical formulation comprises one or more hemiterpenoids. In some embodiments, the pharmaceutical formulation comprises one or more monoterpenoids. In some embodiments, the pharmaceutical formulation comprises one or more sesquitepenoids. In some embodiments, the pharmaceutical formulation comprises one or more sesquitepenoids. In some embodiments, the pharmaceutical formulation comprises one or more diterpenoids. In some embodiments, the pharmaceutical formulation comprises one or more sesterterpenoids. In some embodiments, the pharmaceutical formulation comprises one or more triterpenoids. In some embodiments, the pharmaceutical formulation comprises one or more tetraterpenoids. In some embodiments, the pharmaceutical formulation comprises one or more polyterpenoids. In some embodiments, the pharmaceutical formulation disclosed herein comprises a non-deuterated form of tetrahydrocurcumin. In some embodiments, the pharmaceutical formulation comprises deuterated forms of tetrahydrocurcumin, as described in several embodiments herein. In some embodiments, the pharmaceutical formulation disclosed herein comprises a non-deuterated form of tetrahydrocurcumin and a deuterated form of tetrahydrocurcumin, as described in several embodiments herein.

Half-life, as described herein, refers to the time it takes for a drug or molecule to lose half of its pharmacologic, physiologic, or radiologic activity. The drug or molecule can be a metabolite, signaling molecule, or other substances used for treatment and are known to those skilled in the art. The half-life of a drug in circulation can be affected by kidney function, the liver, and the excretory system that can lead the drug into the metabolic break down by enzymatic reactions in the specific organs of drug passage, and elimination of the drug or molecule from the body of the subject. As drug effectiveness is hampered by its half-life, a higher dosage of drug administered to a subject in need can be implemented, which does not increase half-life, but can be necessary in order to keep the drug in circulation for a longer period of time and would thus be effective in increasing the bioavailability of the drug. However, a higher dose can also be a disadvantage, for example, for some drugs it can lead to toxic effects in higher concentrations of the drug.

In some embodiments, a pharmaceutical formulation or a drug can be administered intravenously. "Intravenous therapy," as described herein, is a route of administration to deliver fluids and medication to a subject in need directly into a vein. However, through this route the bioavailability of a drug can still be affected from enzymatic reactions in the bloodstream.

There are several ways to improve the bioavailability of a drug by methods of increasing the half-life. The development of introducing deuterium into the structure of a molecule to replace hydrogen, can retain the biochemical potency and selectivity of the physiologically active compound and simultaneously modify the metabolic fate in order to increase its bioavailability in the blood stream of a subject in need. Deuteration, or the addition of a deuterium in place of hydrogen, can help to create drugs that can bypass quick metabolizing by the organs of the system compared to their hydrogenated counterparts.

"Deuterium" as described herein is a stable isotope of hydrogen in which the nucleus of deuterium contains one proton and one neutron. The properties of deuterated compounds or molecules can exhibit significant isotope effects and other physical and chemical property differences in comparison to its hydrogenated counterpart. An advantage of deuteration can be the reduced rates of metabolism of a molecule that is deuterated, in the gut wall and or liver. Deuterated drugs or molecules can have a reduced dosing requirement and produce lower metabolite loads. Thereby the deuterated compound can have reduced formation of toxic or reactive metabolites. Although deuterium can behave similarly to hydrogen, deuterium exhibits differences in its bond energy and bond lengths for compounds in which the heavy hydrogen isotopes have replaced hydrogen. For deuterated compounds, the bond length for bound deuterons exceeds that of bound hydrogens. Furthermore, the deuterium-carbon bonds can be six to ten times more stable than that of a carbon-hydrogen bond, lending to a stronger bond that can be more difficult to cleave, thus slowing down the rate of bond cleavage. In effect, this kinetic isotope effect (KIE) can affect the biological fate of drugs that are quickly metabolized by pathways that can involve the cleavage of hydrogen-carbon bonds. In several embodiments, methods are provided for deuteration of a molecule. In some embodiments, pharmaceutical formulations are provided. In some embodiments, the pharmaceutical formulation includes deuterated molecules for treatment. In some embodiments, the pharmaceutical formulation disclosed herein comprises a non-deuterated form of tetrahydrocurcumin. In some embodiments, the pharmaceutical formulation comprises deuterated forms of tetrahydrocurcumin, as described in several embodiments herein. In some embodiments, the pharmaceutical formulation disclosed herein comprises a non-deuterated form of tetrahydrocurcumin and a deuterated form of tetrahydrocurcumin, as described in several embodiments herein.

Curcuminoids are linear diarylheptanoids that are turmeric extracts used as food coloring agents as yellow pigments, and as traditional drugs. However, as a drug curcuminoids have a poor oral bioavailability and low plasma concentration which limits their use. The prominent metabolic pathways for the breakdown of curcuminoids are reduction and conjugation which lead to the molecule being excreted. Several drug metabolizing enzymes such as alcohol dehydrogenase, UDP-glucuronosyltransferases (UGTs) or sulfotransfereases (SULTs) are involved in the metabolic breakdown of curcuminoids. Aside from this pathway, dehydroxylation, cyclization and methylation can also occur in vivo.

"Tetrahydrocurcumin," as described herein, is a major metabolite of the curcuminoid, curcumin and can be used for its anti-fibrotic and anti-oxidant activities. Tetrahydrocurcumin is a strong anti-oxidative molecule, and can be obtained by the hydrogenation of curcumin. Tetrahydrocurcumin can be used as an anti-oxidant in oxidative stress diseases. Although tetrahydrocurcumin is relatively safe at high dosages (80 mgs/kg body weight), one of the major disadvantages of tetrahydrocurcumin is its low solubility, in which it has poor solubility in water at acidic and at physiological pH. Another disadvantage is its ability to hydrolyse rapidly in basic solutions. In a majority of current treatments, tetrahydrocurcumin is poorly absorbed and is rapidly metabolized. In order to increase the half-life of tetrahydrocurcumin, methods are provided for the deuteration of tetrahydrocurcumin. Deuteration at one or two alcohol sites of tetrahydrocurcumin can delay glucuronidation, thus improving the half-life of tetrahydrocurcumin. In some embodiments, a deuterated form of tetrahydrocurcumin is provided. In some embodiments, the deuterated form of tetrahydrocurcumin has at least one deuteron. In some embodiments, the deuterated form of tetrahydrocurcumin has at least five deuterons. In some embodiments, the deuterated form of tetrahydrocurcumin has at least ten deuterons. In some embodiments, the deuterated form of tetrahydrocurcumin has at least fifteen deuterons. In some embodiments, the deuterated form of tetrahydrocurcumin has at least twenty deuterons. In some embodiments, the deuterated form of tetrahydrocurcumin has at least twenty four deuterons.

In some embodiments, a deuterated form of tetrahydrocurcumin is provided. In some embodiments, the deuterated form of tetrahydrocurcumin is deuterated at one site. For example, site 1, site 2, site 3, site 4, site 5, site 6, site 7, site 8, site 9, site 10, site 11, site 12, site 13, site 14 or site 15 can be deuterated.

In some embodiments, tetrahydrocurcumin is deuterated at two sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15. In some embodiments, two of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons.

In some embodiments, tetrahydrocurcumin is deuterated at three sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, three of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at four sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, four of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at five sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, five of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at six sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, six of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at seven sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, seven of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at eight sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, eight of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at nine sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, nine of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at ten sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, ten of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at eleven sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, eleven of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at twelve sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the twelfth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, twelve of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have two deuterons. In some embodiments, site 2 or 12 has three deuterons.

In some embodiments, tetrahydrocurcumin is deuterated at thirteen sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the twelfth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the thirteenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, thirteen of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at fourteen sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the twelfth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the thirteenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourteenth site of deuteration is at site 1, site 2, site 3, site 4, site 5, site 6, site 7, site 8, site 9, site 10, site 11, site 12, site 13, site 14 or site 15. In some embodiments, fourteen of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at fifteen sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the twelfth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the thirteenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourteenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifteenth site of deuteration is at site 1, site 2, site 3, site 4, site 5, site 6, site 7, site 8, site 9, site 10, site 11, site 12, site 13, site 14 or site 15. In some embodiments, fifteen of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

Curcumin is a diarylheptanoid, a class of plant secondary metabolites and can exist in both an enol form and a keto form. Tetrahydrocurcumin is derived from curcumin. Curcumin has been used and studied for its applications as it can have several health benefits, such as anti-carcinogenic, anti-inflammatory, antimicrobial, antioxidant, immunomodulatory, and anti-Alzheimer properties. For example curcumin can be used to reduce hyperlipidemia, delay cataract development, ameliorate renal lesions, treat cancers, immune deficiencies, cardiovascular disease, Alzheimer's diabetes, Crohn's disease, and as an antioxidant curcumin can reduce cross linking of collagen, and reduce blood glucose levels. Like tetrahydrocurcumin, curcumin is poorly absorbed and is rapidly metabolized. To overcome the pharmacological barriers of its low bioavailability, pharmaceutical formulations comprising curcumin as a supplement can also comprise phospholipids to increase absorptivity of curcumin. In some embodiments, the pharmaceutical formulations disclosed herein can comprise curcumin. In some embodiments, the curcumin is deuterated. In some embodiments, curcumin can have one, two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four deuterons.

In some embodiments, the pharmaceutical formulation disclosed herein comprises a non-deuterated form of tetrahydrocurcumin. In some embodiments, the pharmaceutical formulation comprises deuterated forms of tetrahydrocurcumin, as described in several embodiments herein. In some embodiments, the pharmaceutical formulation disclosed herein comprises a non-deuterated form of tetrahydrocurcumin and a deuterated form of tetrahydrocurcumin, as described in several embodiments herein. In some embodiments, the pharmaceutical formulations disclosed herein can comprise a deuterated tetrahydrocurcumin. In some embodiments, the deuterated form of tetrahydrocurcumin is deuterated at two alcohol sites. In some embodiments, the deuterated form of tetrahydrocurcumin has no more than fifteen deuterated sites. In some embodiments, the deuterated form of tetrahydrocurcumin has at least ten deuterated sites. In some embodiments, the deuterated form of tetrahydrocurcumin has at least five deuterated sites. In some embodiments, the deuterated form of tetrahydrocurcumin has at least one deuterated site. In some embodiments, the deuterated form of tetrahydrocurcumin is deuterated at one, two, three, four, five, six, seven, eight, nine, ten, eleven, twelve, thirteen, fourteen, or fifteen sites. The tetrahydrocurcumin can be deuterated, for example, at an alcohol site. In some embodiments, the tetrahydrocurcumin is deuterated at one or two alcohol sites. As shown in FIG. 1, some deuteration sites can have one, two, or three deuterons. For example, in FIG. 1, deuteration site 1 can have one deuteron; deuteration site 2 refers to the methyl group which can have one, two or three deuterons (e.g., deuteration sites 2a, 2b, and 2c); deuteration site 12 refers to the methyl group which can have one, two or three deuterons (deuteration sites 12a, 12b, and 12c); deuteration sites 6, 7, 8, 9 and 10 can have one or two deuterons (deuteration sites 6a and 6b, 7a and 7b, 8a and 8b, 9a and 9b, and 10a and 10b). The two alcohol sites of tetrahydrocurcumin at sites 3 and 13 are sites that can increase the half-life of tetrahydrocurcumin. In some embodiments, the deuterated form of tetrahydrocurcumin is deuterated at sites 3 and 13.

Tetrahydrocurcumin has fifteen deuteration sites, some of which can have one, two or three deuterons. In some embodiments, the deuterated form of tetrahydrocurcumin has at least one deuteron. In some embodiments, the deuterated form of tetrahydrocurcumin has at least five deuterons. In some embodiments, the deuterated form of tetrahydrocurcumin has at least ten deuterons. In some embodiments, the deuterated form of tetrahydrocurcumin has at least fifteen deuterons. In some embodiments, the deuterated form of tetrahydrocurcumin has at least twenty deuterons. In some embodiments, the deuterated form of tetrahydrocurcumin has at least twenty-four deuterons. In some embodiments, the deuterated form of tetrahydrocurcumin has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four deuterons.

In some embodiments, a pharmaceutical formulation comprising a deuterated form of tetrahydrocurcumin is provided. In some embodiments, the pharmaceutical formulation comprises a pharmaceutical vehicle. "Pharmaceutical vehicle" as described herein refers to an inert substance with which a medication is mixed to facilitate measurement and administration of the pharmaceutical formulation. In some embodiments the tetrahydrocurcumin is deuterated. In some embodiments, the deuterated form of tetrahydrocurcumin is deuterated at one site. For example, site 1, site 2, site 3, site 4, site 5, site 6, site 7, site 8, site 9, site 10, site 11, site 12, site 13, site 14 or site 15 can be deuterated.

In some embodiments, pharmaceutical formulations disclosed herein can comprise tetrahydrocurcumin deuterated at two sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15. In some embodiments, two of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons.

In some embodiments, pharmaceutical formulations disclosed herein can comprise tetrahydrocurcumin deuterated at three sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, three of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, pharmaceutical formulations disclosed herein can comprise tetrahydrocurcumin deuterated at four sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, four of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, pharmaceutical formulations disclosed herein can comprise tetrahydrocurcumin deuterated at five sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, five of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, pharmaceutical formulations disclosed herein can comprise tetrahydrocurcumin deuterated at six sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, six of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, pharmaceutical formulations disclosed herein can comprise tetrahydrocurcumin deuterated at seven sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, seven of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, pharmaceutical formulations disclosed herein can comprise tetrahydrocurcumin deuterated at eight sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, eight of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, pharmaceutical formulations disclosed herein can comprise tetrahydrocurcumin deuterated at nine sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, nine of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, pharmaceutical formulations disclosed herein can comprise tetrahydrocurcumin deuterated at ten sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, ten of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, pharmaceutical formulations disclosed herein can comprise tetrahydrocurcumin deuterated at eleven sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, eleven of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, pharmaceutical formulations disclosed herein can comprise tetrahydrocurcumin deuterated at twelve sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the twelfth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, twelve of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have two deuterons. In some embodiments, site 2 or 12 has three deuterons.

In some embodiments, pharmaceutical formulations disclosed herein can comprise tetrahydrocurcumin deuterated at thirteen sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the twelfth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the thirteenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, thirteen of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, pharmaceutical formulations disclosed herein can comprise tetrahydrocurcumin deuterated at fourteen sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the twelfth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the thirteenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourteenth site of deuteration is at site 1, site 2, site 3, site 4, site 5, site 6, site 7, site 8, site 9, site 10, site 11, site 12, site 13, site 14 or site 15. In some embodiments, fourteen of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, pharmaceutical formulations disclosed herein can comprise tetrahydrocurcumin deuterated at fifteen sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the twelfth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the thirteenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourteenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifteenth site of deuteration is at site 1, site 2, site 3, site 4, site 5, site 6, site 7, site 8, site 9, site 10, site 11, site 12, site 13, site 14 or site 15. In some embodiments, fifteen of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

Pharmaceutical Formulations

In some embodiments, the active ingredients and mixtures of active ingredients can be used, for example, in pharmaceutical formulations comprising a pharmaceutically acceptable carrier prepared for storage and subsequent administration. Also, some embodiments include use of the above-described active ingredients with a pharmaceutically acceptable carrier or diluent. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes and even flavoring agents can be provided in the pharmaceutical formulation. For example, sodium benzoate, ascorbic acid and esters of p-hydroxybenzoic acid can be added as preservatives. In addition, antioxidants and suspending agents can be used.

Pharmaceutical formulations of the active ingredients can be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical formulations can contain minor amounts of nontoxic auxiliary substances, such as wetting agents, pH buffering agents, and the like. If desired, absorption enhancing preparations (for example, liposomes), can be utilized.

For injection, the agents of the invention can be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the ingredients herein disclosed for the practice of the invention into dosages suitable for systemic administration is within the scope of the invention. With proper choice of carrier and suitable manufacturing practice, the pharmaceutical formulations disclosed herein, in particular, those formulated as solutions, can be administered parenterally, such as by intravenous injection. The active ingredients can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical formulations for parenteral administration include aqueous solutions of the active ingredients in water-soluble form. Additionally, suspensions of the active ingredients can be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents that increase the solubility of the ingredients to allow for the preparation of highly concentrated solutions. In some embodiments, of the pharmaceutical formulations, the vehicle is a lipophilic solvent, fatty oil, organic oil, or liposome. In some embodiments, the vehicle is sesame oil, soybean, grapefruit or almond oils, or synthetic fatty acid esters, such as ethyl oleate or triglycerides, or liposomes.

Pharmaceutical preparations for oral use can be obtained by combining the active ingredients with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active ingredient doses. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active ingredient doses. Such formulations can be made using methods known in the art. See, for example, U.S. Pat. No. 5,733,888 (injectable pharmaceutical formulations); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations); all of which are incorporated herein by reference in their entireties. The pharmaceutical formulations can be manufactured in a manner that is itself known, for example, by means of conventional mixing, dissolving, granulating, dragee-making, levitating, emulsifying, encapsulating, entrapping, or lyophilizing processes. In some embodiments, the pharmaceutical formulation further comprises an excipient. In some embodiments, the pharmaceutical formulation is prepared for oral use. In some embodiments, the excipient is sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

To formulate the dosage including one or more active ingredients disclosed herein, known surface active agents, excipients, smoothing agents, suspension agents and pharmaceutically acceptable film-forming substances and coating assistants, and the like can be used. Preferably alcohols, esters, sulfated aliphatic alcohols, and the like can be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like can be used as excipients; magnesium stearate, talc, hardened oil and the like can be used as smoothing agents; coconut oil, olive oil, sesame oil, peanut oil, soya can be used as suspension agents or lubricants; cellulose acetate phthalate as a derivative of a carbohydrate such as cellulose or sugar, or methylacetate-methacrylate copolymer as a derivative of polyvinyl can be used as suspension agents; and plasticizers such as ester phthalates and the like can be used as suspension agents. In addition to the foregoing ingredients, sweeteners, fragrances, colorants, preservatives and the like can be added to the administered formulation of the compound of the invention, particularly when the compound is to be administered orally.

Further disclosed herein are various pharmaceutical formulations well known in the pharmaceutical art for uses that include intraocular, intranasal, and intraauricular delivery. Pharmaceutical formulations include aqueous ophthalmic solutions of the active ingredients in water-soluble form, such as eyedrops, or in gellan gum (Shedden et al., Clin. Ther., 23(3):440-50 (2001)) or hydrogels (Mayer et al., Ophthalmologica, 210(2):101-3 (1996)); ophthalmic ointments; ophthalmic suspensions, such as microparticulates, drug-containing small polymeric particles that are suspended in a liquid carrier medium (Joshi, A., J. Ocul. Pharmacol., 10(1): 29-45 (1994)), lipid-soluble formulations (Alm et al., Prog. Clin. Biol. Res., 312:447-58 (1989)), and microspheres (Mordenti, Toxicol. Sci., 52(1):101-6 (1999)); and ocular inserts. All of the above-mentioned references are incorporated herein by reference in their entireties. Such suitable pharmaceutical formulations are most often and preferably formulated to be sterile, isotonic and buffered for stability and comfort. Pharmaceutical formulations can also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The pharmaceutical formulations described herein can be administered by either oral or non-oral pathways. When administered orally, pharmaceutical formulations can be administered in capsule, tablet, granule, spray, syrup, or other such form. Pharmaceutical formulations also can be brewed, as with a tea, or formed by dissolving a powdered pharmaceutical formulation into a fluid, typically water, fruit or vegetable juice, or milk. When administered non-orally, it can be administered as an aqueous suspension, an oily preparation or the like or as a drip, suppository, salve, ointment or the like, when administered via injection, subcutaneously, intreperitoneally, intravenously, intramuscularly, or the like. Similarly, it can be administered topically, rectally, or vaginally, as deemed appropriate by those of skill in the art for bringing the ingredients of the invention into optimal contact with living tissue.

Agents intended to be administered intracellularly can be administered using techniques well known to those of ordinary skill in the art. For example, such agents can be encapsulated into liposomes, then administered by any of the methods described herein. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules can be directly administered intracellularly.

In some embodiments, the pharmaceutical formulations described herein are formulated into a single pill or tablet. In some embodiments, the pill or tablet has a mass from 10 mg to 2000 mg. In some embodiments, the pill or tablet has a mass from 100 mg to 1500 mg. In some embodiments, the pill or tablet has a mass from 500 mg to 1200 mg. In some embodiments, the pill or tablet has a mass from 800 mg to 1100 mg.

Methods of Administration

Some embodiments also encompass methods for making and for administering the disclosed pharmaceutical formulations. Such disclosed methods include, among others, (a) administration through oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the invention into contact with living tissue; and (f) administration via controlled released formulations, depot formulations, and infusion pump delivery. As further examples of such modes of administration and as further disclosure of modes of administration, disclosed herein are various methods for administration of the disclosed pharmaceutical formulations including modes of administration through intraocular, intranasal, and intraauricular pathways.

The pharmaceutically effective amount of the ingredients disclosed herein required as a dose will depend on the route of administration and the physical characteristics of the specific human under consideration. The dose can be tailored to achieve a desired effect, but will depend on such factors as weight, diet, concurrent medication and other factors, which those skilled in the medical arts will recognize.

In practicing the methods of the invention, the products or pharmaceutical formulations can be used alone or in combination with one another or in combination with other therapeutic or diagnostic agents. These products can be utilized in vivo, ordinarily in a mammal, preferably in a human, or in vitro. In employing them in vivo, the products or pharmaceutical formulations can be administered to the mammal in a variety of ways, including parenterally, intravenously, subcutaneously, intramuscularly, colonically, rectally, vaginally, nasally or intraperitoneally, employing a variety of dosage forms. Such methods can also be applied to testing chemical activity in vivo.

As will be readily apparent to one skilled in the art, the useful in vivo dosage to be administered and the particular mode of administration will vary depending upon the age, weight and mammalian species treated, the particular ingredients employed, and the specific use for which these ingredients are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the pharmaceutical formulations identified by the present methods using established pharmacological methods. In non-human animal studies, applications of potential products are commenced at higher dosage levels, with dosage being decreased until the desired effect is no longer achieved or adverse side effects disappear.

The dosage of active ingredient(s) can range broadly, depending upon the desired affects and the therapeutic indication. Typically, dosages of active ingredient(s) can be between about 10 microgram/kg and 100 mg/kg body weight, preferably between about 100 microgram/kg and 10 mg/kg body weight. Alternatively dosages can be based and calculated upon the surface area of the patient, as understood by those of skill in the art. Administration is preferably oral on a daily or twice daily basis. In some embodiments, the active ingredient in the pharmaceutical formulation of any of the embodiments described herein is non-deuterated or deuterated form of tetrahydrocurcumin. In some embodiments, the active ingredient(s) can be between about 10 microgram/kg and 100 mg/kg body weight, preferably between about 100 microgram/kg and 10 mg/kg body weight.

The exact formulation, route of administration and dosage can be chosen in view of the consumer's condition. See for example, Fingl et al., in The Pharmacological Basis of Therapeutics, 1975, which is incorporated herein by reference in its entirety. The magnitude of an administrated dose can vary with the severity of a particular medical or physical condition and the route of administration. The severity of a condition can, for example, be evaluated, in part, by standard prognostic evaluation methods. Further, the dose and perhaps dose frequency can also vary according to the age, body weight, and response of the individual. A program comparable to that discussed herein can be used in veterinary medicine.

A variety of techniques for formulation and administration can be found in Remington's Pharmaceutical Sciences, 18th Ed., Mack Publishing Co., Easton, Pa. (1990), which is incorporated herein by reference in its entirety. Suitable administration routes can include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

The combined active ingredients in the pharmaceutical formulations disclosed herein can be orally or non-orally administered to a human patient in the amount of about 0.0007 mg/day to about 7,000 mg/day of the total active ingredients, and more preferably about 0.07 mg/day to about 70 mg/day of the total active ingredients at, one time per day or in other embodiments, over two to about ten times per day. Alternatively, the active ingredients disclosed herein can be administered in the stated amounts continuously by, for example, an intravenous drip. Thus, for a patient weighing 70 kilograms, the preferred daily dose of the total active ingredients would be about 0.0007 mg/kg/day to about 35 mg/kg/day, and more preferable, 0.007 mg/kg/day to about 15 mg/kg/day. Nonetheless, as will be understood by those of skill in the art, in certain situations it can be necessary to administer the active ingredients disclosed herein in amounts that excess, or even far exceed, the above-stated, preferred dosage range to treat effectively and aggressively a desired condition or characteristic.

In some embodiments, the pharmaceutical formulations disclosed herein can be orally or non-orally administered to a human patient in the amount of about 0.0007 mg/day to about 7,000 mg/day of the total active ingredients, and more preferably about 0.07 mg/day to about 70 mg/day of the total active ingredients at, one time per day or in other embodiments, over two to about ten times per day. In some embodiments, the preferred daily dose of the total active ingredients would be about 0.0007 mg/kg/day to about 35 mg/kg/day, and more preferable, 0.007 mg/kg/day to about 15 mg/kg/day.

Ingredients disclosed herein can be evaluated for efficacy and toxicity using known methods. For example, the toxicology of a particular compound or ingredient, or of a subset of the compounds, sharing certain chemical moieties, can be established by determining in vitro toxicity towards a cell line, such as a mammalian, and preferably a human, cell line. The results of such studies are often predictive of toxicity in animals, such as mammals, or more specifically, humans. Alternatively, the toxicity of particular compounds or ingredients in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including the conditions abated by the compounds or ingredients disclosed herein, including obesity. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound or ingredient in humans.

The active ingredients described herein may be used alone or in combination with one another, or in combination with other therapeutic or diagnostic agents. These products can be utilized in vivo or in vitro. The useful dosages and the most useful modes of administration will vary depending upon the age and weight of the consumer, the particular ingredients employed, and the specific use for which these ingredients are employed.

In some embodiments, a method for making deuterated tetrahydrocurcumin is provided. The concept of deuteration of tetrahydrocurcumin is similar to that of the deuteration of dimethylcurcumin, in which the deuteration concept is described, for example, in U.S. Pat. No. 8,575,221 B2, which is hereby incorporated by reference in its entirety. The method can comprise contacting tetrahydrocurcumin in the presence of a catalyst and deuterated water under a condition to form the deuterated form of tetrahydrocurcumin. The method can further comprise hydrogenating curcumin to form the tetrahydrocurcumin. In some embodiments, the deuterated form of tetrahydrocurcumin has at least one deuterated site. In some embodiments, the deuterated form of tetrahydrocurcumin has at least five deuterated sites. In some embodiments, the deuterated form of tetrahydrocurcumin has at least ten deuterated sites. In some embodiments, the deuterated form of tetrahydrocurcumin has fifteen deuterated sites or an amount less fifteen deuterated sites. In some embodiments, the deuterated form of tetrahydrocurcumin is deuterated at one or two alcohol sites. In some embodiments, the deuterated form of tetrahydrocurcumin has one, two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four deuterons. In some embodiments, the deuterated form of tetrahydrocurcumin is deuterated at one or two alcohol sites.

In some embodiments, a method for making deuterated tetrahydrocurcumin is provided. In some embodiments, tetrahydrocurcumin is deuterated at one site. In some embodiments, site 1, site 2, site 3, site 4, site 5, site 6, site 7, site 8, site 9, site 10, site 11, site 12, site 13, site 14 or site 15 is deuterated.

In some embodiments, tetrahydrocurcumin is deuterated at two sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15. In some embodiments, two of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons.

In some embodiments, tetrahydrocurcumin is deuterated at three sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, three of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at four sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, four of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at five sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, five of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at six sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, six of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at seven sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, seven of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at eight sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, eight of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at nine sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, nine of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at ten sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, ten of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at eleven sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, eleven of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at twelve sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the twelfth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, twelve of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have two deuterons. In some embodiments, site 2 or 12 has three deuterons.

In some embodiments, tetrahydrocurcumin is deuterated at thirteen sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the twelfth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the thirteenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, thirteen of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at fourteen sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the twelfth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the thirteenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourteenth site of deuteration is at site 1, site 2, site 3, site 4, site 5, site 6, site 7, site 8, site 9, site 10, site 11, site 12, site 13, site 14 or site 15. In some embodiments, fourteen of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, tetrahydrocurcumin is deuterated at fifteen sites. In some embodiments, at least one of site 1, site 2, site 3, site 4, site 5, site 6, site 7, site 8, site 9, site 10, site 11, site 12, site 13, site 14 and site 15 in the deuterated form of tetrahydrocurcumin is deuterated. In some embodiments, the second site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the third site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the sixth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the seventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eighth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the ninth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the tenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the eleventh site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the twelfth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the thirteenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fourteenth site of deuteration is at site 1, site 2, site 3, site 4, site 5, site 6, site 7, site 8, site 9, site 10, site 11, site 12, site 13, site 14 or site 15 in the deuterated form of tetrahydrocurcumin. In some embodiments, the fifteenth site of deuteration is at site 1, site 2, site 3, site 4, site 5, site 6, site 7, site 8, site 9, site 10, site 11, site 12, site 13, site 14 or site 15. In some embodiments, fifteen of site 1, site 2, site 3, site 4, site 5, site 6, site 7, site 8, site 9, site 10, site 11, site 12, site 13, site 14 and site 15 in the deuterated form of tetrahydrocurcumin are deuterated. In some embodiments, a deuterated site in the deuterated form of tetrahydrocurcumin can have two deuterons. In some embodiments, site 2, 6, 7, 8, 9, 10, or 12 has two deuterons. In some embodiments, a deuterated site in the deuterated form of tetrahydrocurcumin can have three deuterons. In some embodiments, site 2 or 12 has three deuterons.

In some embodiments, the method can include a metal catalyst. Examples of metal catalysts include but are not limited to palladium on carbon, palladium barium carbonate, palladium barium sulphate, palladium silica, palladium alumina, platinum on carbon, platinum-palladium carbon, platinum alumina, platinum calcium carbonate, platinum barium sulfate, platinum silica, and platinum graphite. In some embodiments, the deuterated water can be 25% deuterated, 50% deuterated, 75% deuterated, 100% deuterated, or any other value between any of these values. In some embodiments, the catalyst is palladium on carbon. In some embodiments, the catalyst is palladium barium carbonate. In some embodiments, the catalyst is palladium barium sulphate. In some embodiments, the catalyst is palladium silica. In some embodiments, the catalyst is platinum on carbon. In some embodiments, the catalyst is platinum-palladium carbon. In some embodiments, the catalyst is platinum alumina. In some embodiments, the catalyst is platinum calcium carbonate. In some embodiments, the catalyst is platinum barium sulfate. In some embodiments, the catalyst is platinum silica. In some embodiments, the catalyst is platinum graphite. In some embodiments, the deuterated water is at least 25% deuterated. In some embodiments, the deuterated water is at least 50% deuterated. In some embodiments, the deuterated water is at least 75% deuterated. In some embodiments, the deuterated water is 100% deuterated.

Purification of tetrahydrocurcumin can be performed to remove the byproducts produced from the hydrogenation of curcumin. Separation of tetrahydrocurcumin can be performed, for example, by column chromatography. Column chromatography can include techniques such as reverse phase HPLC. In some embodiments, tetrahydrocurcumin is purified by column chromatography. The methods of synthesis of deuterated tetrahydrocurcumin can be prepared by a person skilled in the art using procedures with appropriate concentrations of deuterated reagents. In some embodiments, the curcumin is hydrogenated to tetrahydrocurcumin followed by deuteration. Additional methods for synthesizing deuterated tetrahydrocurcumin that are not schematically shown herein are known to persons skilled in the art. In some embodiments, the method further comprises purifying the deuterated form of tetrahydrocurcumin. In some embodiments, the purifying step comprises isolating the deuterated form of tetrahydrocurcumin with column chromatography.

The anti-oxidant effects of tetrahydrocurcumin can be used for atherosclerotic lesion, several types of cancers, prevention of type II diabetes, and protection of organs from oxidative damage, such as the heart, kidney and liver. Without being limiting, several cancers can include, basal cell carcinoma, bile duct cancer, bone cancer, brain stem glioma, breast cancer, Burkitt Lymphoma, cervical cancer, colon cancer, colorectal cancer, cutaneous T-cell lymphoma, ductal carcinoma, endometrial cancer, esophageal cancer, Ewing sarcoma, retinoblastoma, gallbladder cancer, gastric cancer, kidney cancer, liver cancer, pancreatic cancer, leukemia, lung cancer, melanoma, ovarian cancer, skin cancer, and stomach cancer. In some embodiments, the non-deuterated or deuterated form of tetrahydrocurcumin in a pharmaceutical formulation can be used to treat atherosclerotic lesion, several types of cancers or type II diabetes as a therapy.

"Atherosclerosis" as described herein, refers to the thickening of the artery wall which can be the results of dead cells, damage from high cholesterol, triglycerides, and plaques. Atherosclerosis can lead to the atherosclerotic lesions cab be considered advanced when there are a high accumulation of lipid, cells, and matrix pharmaceutical formulations which can narrow the arterial lumen and become clinically significant, leading to complications. In some embodiments, methods are provided for treating, inhibiting, or ameliorating a disorder in a subject. In some embodiments, the subject suffers from atherosclerosis.

Cancer can refer to a group of diseases that can involve abnormal cell growth that invades and spreads within a body. To date there are over one hundred types of cancer, in which systems and states depend upon the type of cancer. Current treatment for cancer can include chemotherapy, radiation, drug therapy, and surgical procedures. The anti-oxidant effect of tetrahydrocurcumin can be used to treat several types of cancers. In some embodiments, methods are provided for treating, inhibiting, or ameliorating a disorder in a subject. In some embodiments, the subject suffers from cancer.

"Type II diabetes," as described herein refers to a metabolic disorder that is characterized by hyperglycemia, insulin resistance, and the relative lack of insulin. Subjects suffering from Type II diabetes can synthesize insulin, however either the pancreas cannot make enough insulin, or the body of the subject cannot use insulin. Insulin resistance can refer to the lack of insulin or the inability to use the insulin, leading to a high level of glucose in the blood leading to detrimental effects in the subject. High levels of blood sugar can lead to nerve damage, small blood vessel damage, organ damage, atherosclerosis, arterial hardening, heart attack and stroke. Type II diabetes with hyperlipidemia, can involve abnormally elevated levels of lipids and lipoproteins in the blood which can be due to genetic causes. In diabetes, the liver and the kidney play a major role in the pathogenesis of the disease. The liver enzymes aspartate transaminase, alanine transaminase, alkaline phosphates, and γ-glutamyl transpeptidase are used for assessing liver function, in which they are elevated in patients with liver diseases. In some embodiments, methods are provided for treating, inhibiting, or ameliorating a disorder in a subject. In some embodiments, the subject suffers from Type II diabetes.

In several studies, tetrahydrocurcumin was shown to decrease the levels of plasma total protein, albumin, globulin and albumin/globulin ratio. Additionally, hepatic and renal markers that are elevated in diabetic mice were significantly lowered in the presence of tetrahydrocurcumin. Administration of tetrahydrocurcumin can normalize blood glucose and cause an improvement of altered carbohydrate metabolic enzymes. Furthermore, tetrahydrocurcumin can cause a significant increase in the activities of superoxide dismutase, catalase, glutathione peroxidase, glutathione S-transferase, reduced glutathione, vitamin C and vitamin E in the liver or diabetic rats, indicating a role of tetrahydrocurcumin in preventing lipid peroxidation induced membrane damage. More importantly tetrahydrocurcumin has been shown to have an antioxidant effect in addition to an anti-diabetic effect in Type II diabetes. In view of tetrahydrocurcumins potential compared to Silymarin, a liver protective substance known to increase glutathione production in the liver, tetrahydrocurcumin was shown to have better protection against lipid peroxidation. However in view of the bioavailability of tetrahydrocurcumin and curcumin and their ability to be quickly metabolized, improved pharmaceutical formulations are needed in order to allow absorption and stability in a subject being treated, to avoid rapid metabolizing of the drug before it reaches its target organ. In some embodiments, treating, inhibiting, or ameliorating a disorder in a subject is provided. A disorder, as used herein, can refer to a condition that interferes with cells, tissues, and organs. In some embodiments, the subject suffers from diabetes. In some embodiments, the subject suffers from Type II diabetes with hyperlipidemia.

"Hypertension," as described herein, is a chronic medical condition in which blood pressure in the arteries is elevated.

Hypertension puts strain on the heart and can lead to hypertensive heart disease, and coronary heart disease. Hypertension can lead to stroke, aneurysms, peripheral arterial disease and can be a causative factor for chronic kidney disease. Left ventricular hypertrophy in hypertension can reflect physiological adaptation to increased work load of the heart and is a strong risk factor for future cardiac events such as sudden cardiac death. ROS and oxidative stress can also lead into the genesis of hypertension due to hypertensive stimuli which can also promote the production of ROS in the brain, kidney and vasculature structure. In some embodiments, methods are provided for treating, inhibiting, or ameliorating a disorder in a subject. In some embodiments, the subject suffers from hypertension. In some embodiments, the subject suffers from hypertension with left ventricular hypertrophy. Galectin-3, as described herein, is a protein lectin that has been demonstrated to be involved in pulmonary hypertension, hypertension, cancer, inflammation, fibrosis, heart disease and stroke. In some embodiments, the subject has elevated Galectin-3 levels in the blood. In some embodiments, the subject has heart failure. In some embodiments, the subject has heart disease.

Oxidative damage in a subject can refer to damage that is caused by the presence of reactive oxygen species (ROS) and the inability of a biological system to detoxify the reactive intermediates or repair the resulting damage. The production of peroxides and free radicals can cause damage to major components of a biological system and can include but is not limited to proteins, lipids, DNA, RNA, tissues, and organs. Organs can also be damaged by the effects of ROS and other types of free radical production leading to organ atrophy and organ dysfunction. Organs can include but are not limited to the heart, lung, kidney, liver, brain and abdominal organs. In some embodiments, methods are provided for protecting an organ in a subject. In some embodiments, the organ is kidney. In some embodiments, the organ is liver. In some embodiments, the subject has a liver disorder. In some embodiments, the subject has a fatty liver disease. In some embodiments, the subject has alcoholic liver disease. In some embodiments, the subject has a kidney disease. In some embodiments, the subject has diabetic kidney disease. In some embodiments, the subject has polycystic kidney disease. In some embodiments, the subject has heart failure.

Reactive oxygen species has also been implicated in multiple pathologies such as hypertension, atherosclerosis, and diabetes. In some embodiments, the subject has hypertension. In some embodiments, the subject has hypertension with left ventricular hypertrophy. In some embodiments, the subject has diabetes. In some embodiments, the subject has diabetes with hyperlipidemia. In some embodiments, the subject has elevated levels of fibrotic markers. In some embodiments, the fibrotic markers are in blood. In some embodiments, the fibrotic markers are in urine. In some embodiments, the subject has elevated markers of oxidative stress. The reactive oxidative stress can be involved in diseases, cancers, Parkinson's disease, Alzheimer's disease, atherosclerosis, heart failure, vitiligo, and chronic fatigue syndrome. Oxidative stress can be caused by the excess generation of ROS, free radical production, or a decrease in endogenous antioxidant defenses. ROS and reactive nitrogen species (RNS) can be the products of cellular metabolism and other sources of stress that together can serve as deleterious or even beneficial species, for example the increase of free radicals to stimulate an immune response. Oxidative stress that can lead to the production of free radicals can be caused by many factors, for example, excessive exercise, diet, medications, glycation, diseases, environment, toxins, excessive alcohol consumption, long term smoking, diabetes, cancers, and autoimmune diseases. For example, in the case of diabetes, free radicals can be formed by glucose oxidation, non-enzymatic glycation of proteins, and oxidative degradation of glycated proteins. The abnormally high level of free radicals and decline of an antioxidant defense system can thus lead to damage of cellular proteins and organelles, increase in lipid peroxidation and the development of insulin resistance.

Tetrahydrocurcumin can be used to treat renal damage, hepatotoxicity, and hepatic damage. Damage to the renal and hepatic tissue can occur from analgesics, cancers, free radical damage, and long-term drug use, for example treatment for malaria. However, due to the low bioavailability of curcuminoids such as curcumin and tetrahydrocurcumin, the drugs are easily passed through the system and rapidly metabolized as well. In embodiments described herein, methods are provided for treating organ damage. In some embodiments, organ damage can arise from analgesics, cancers, free radical damage, and long-term drug use such as use of anti-malarial drugs. In some embodiments, methods are provided for treating, inhibiting, or ameliorating a disorder in a subject. In some embodiments, the subject suffers from renal damage. In some embodiments, the subject suffers from hepatic damage. In some embodiments, the subject suffers from hepatotoxicity. In some embodiments, the subject is human. In some embodiments, the subject is taking analgesics. In some embodiments, the subject is under treatment with one or more anti-malarial drugs.

Subjects experiencing the damage caused by ROS or other types of free radical species can be identified through the identification of higher levels of oxidative stress biomarkers. Examples of biomarkers for oxidative stress include but are not limited to superoxide dismutase, catalase, glutathione reductase, glutathione peroxidase, glutathione levels, vitamins, lipid peroxidation, nitrate concentration, non-enzymatic glycosylated proteins, Galectin-3, markers of inflammation, fibrotic markers, lipid hydroperoxides, thiobarbituric acid reactive substances, malondialdehyde, free F2-IsoPs, dityrosine and 8-hydroxy-2'-deoxyguanosine. Examples of markers for inflammation include but are not limited to s100B, α1-anti-chymotrypsin, IL-8, IL-1β, macrophage inflammatory protein-1α, macrophage migration inhibitory factor, granulocyte-macrophage colony-stimulating factor and TNF-α. Examples of fibrotic markers include but are not limited to matrix metalloproteinases and hyaluronic acid, pro-inflammatory and pro-fibrotic cytokines, such as tumor necrosis factor-α (TNF-α), transforming growth factor-β, KL-6, SP-A, MMP-7, and CCL-18.

In some embodiments, a method of treating, inhibiting, or ameliorating a disorder in a subject is provided. In some embodiments, the subject has elevated Galectin-3 levels in the blood. In some embodiments, the subject has elevated levels of fibrotic markers. In some embodiments, the fibrotic markers are in blood. In some embodiments, the fibrotic markers are in urine. In some embodiments, the subject has an elevated level of a marker of oxidative stress. In some embodiments, the marker of oxidative stress is in blood. In some embodiments, the marker of oxidative stress is in urine. In some embodiments, the subject has an elevated level of a marker of inflammation. In some embodiments, the marker of inflammation is in blood. In some embodiments, the marker of inflammation is in urine.

In some embodiments, a method of protecting an organ is provided. In some embodiments, the method comprises identifying a subject in need of protection of an organ and administering a pharmaceutical formulation according to any of the embodiments described herein to a subject in need. In some embodiments, the organ is heart. In some embodiments, the organ is liver. In some embodiments, the organ is kidney. In some embodiments, the subject has elevated Galectin-3 levels in the blood. In some embodiments, the subject has elevated levels of fibrotic markers. In some embodiments, the fibrotic markers are in blood. In some embodiments, the fibrotic markers are in urine. In some embodiments, the subject has an elevated level of a marker of oxidative stress. In some embodiments, the marker of oxidative stress is in blood. In some embodiments, the marker of oxidative stress is in urine. In some embodiments, the subject has an elevated level of a marker of inflammation. In some embodiments, the marker of inflammation is in blood. In some embodiments, the marker of inflammation is in urine.

In several embodiments, herein, methods are provided for treating, inhibiting, or ameliorating a disorder in a subject comprising administering a pharmaceutical formulation of any of the embodiments described herein, comprising a non-deuterated form of tetrahydrocurcumin. In some embodiments, the subject has elevated biomarkers for oxidative stress. In some embodiments, the tetrahydrocurcumin in the pharmaceutical formulation is not deuterated. In several embodiments, herein, methods are provided for treating, inhibiting, or ameliorating a disorder in a subject comprising administering a pharmaceutical formulation of any of the embodiments described herein, comprising a non-deuterated form of tetrahydrocurcumin. In some embodiments, the subject has an elevated biomarker for Galectin-3. In several embodiments herein, methods are provided for treating, inhibiting, or ameliorating a disorder in a subject comprising administering a pharmaceutical formulation of any of the embodiments described herein, comprising a non-deuterated form of tetrahydrocurcumin. In some embodiments, the subject has elevated biomarkers for oxidative stress. In several embodiments, herein, methods are provided for treating, inhibiting, or ameliorating a disorder in a subject comprising administering a pharmaceutical formulation of any of the embodiments described herein, comprising a non-deuterated form of tetrahydrocurcumin. In some embodiments, the subject has elevated fibrotic markers. In several embodiments, herein, methods are provided for treating, inhibiting, or ameliorating a disorder in a subject comprising administering a pharmaceutical formulation of any of the embodiments described herein, comprising a non-deuterated form of tetrahydrocurcumin. In some embodiments, the subject has elevated inflammation markers. In several embodiments, herein, methods are provided for treating, inhibiting, or ameliorating a disorder in a subject comprising administering a pharmaceutical formulation of any of the embodiments described herein, comprising a non-deuterated form of tetrahydrocurcumin. In some embodiments, the subject has elevated inflammation markers. In some embodiments, the pharmaceutical formulation disclosed herein comprises a non-deuterated form of tetrahydrocurcumin. In some embodiments, the pharmaceutical formulation comprises deuterated forms of tetrahydrocurcumin, as described in several embodiments herein. In some embodiments, the pharmaceutical formulation disclosed herein comprises a non-deuterated form of tetrahydrocurcumin and a deuterated form of tetrahydrocurcumin, as described in several embodiments herein. In some embodiments, the pharmaceutical formulation further comprises a supplement. In some embodiments, the supplement is curcumin. In some embodiments, the curcumin is deuterated. In some embodiments, the curcumin is non-deuterated. In some embodiments, there are non-deuterated and deuterated forms of curcumin in the pharmaceutical formulation. In some embodiments, the supplement is a terpenoid. In some embodiments, the supplement is an antioxidant.

In several embodiments, herein, methods are provided for treating, inhibiting, or ameliorating a disorder in a subject comprising administering a pharmaceutical formulation of any of the embodiments described herein, comprising a deuterated form of tetrahydrocurcumin. In some embodiments, the subject has elevated biomarkers for oxidative stress. In several embodiments, herein, methods are provided for treating, inhibiting, or ameliorating a disorder in a subject comprising administering a pharmaceutical formulation of any of the embodiments described herein, comprising a deuterated form of tetrahydrocurcumin. In some embodiments, the subject has an elevated biomarker for Galectin-3. In several embodiments herein, methods are provided for treating, inhibiting, or ameliorating a disorder in a subject comprising administering a pharmaceutical formulation of any of the embodiments described herein, comprising a deuterated form of tetrahydrocurcumin. In some embodiments, the subject has elevated biomarkers for oxidative stress. In several embodiments, herein, methods are provided for treating, inhibiting, or ameliorating a disorder in a subject comprising administering a pharmaceutical formulation of any of the embodiments described herein, comprising a deuterated form of tetrahydrocurcumin. In some embodiments, the subject has elevated fibrotic markers. In several embodiments, herein, methods are provided for treating, inhibiting, or ameliorating a disorder in a subject comprising administering a pharmaceutical formulation of any of the embodiments described herein, comprising a deuterated form of tetrahydrocurcumin. In some embodiments, the subject has elevated inflammation markers. In several embodiments, herein, methods are provided for treating, inhibiting, or ameliorating a disorder in a subject comprising administering a pharmaceutical formulation of any of the embodiments described herein, comprising a deuterated form of tetrahydrocurcumin. In some embodiments, the subject has elevated inflammation markers. In some embodiments, the pharmaceutical formulation comprises one or more forms of deuterated tetrahydrocurcumin. In some embodiments, the pharmaceutical formulation disclosed herein comprises a non-deuterated form of tetrahydrocurcumin. In some embodiments, the pharmaceutical formulation comprises deuterated forms of tetrahydrocurcumin, as described in several embodiments herein. In some embodiments, the pharmaceutical formulation disclosed herein comprises a non-deuterated form of tetrahydrocurcumin and a deuterated form of tetrahydrocurcumin, as described in several embodiments herein. In some embodiments, the pharmaceutical formulation further comprises a supplement. In some embodiments, the supplement is curcumin. In some embodiments, the curcumin is deuterated. In some embodiments, the supplement is a terpenoid. In some embodiments, the supplement is an antioxidant.

For example, it has also been shown that tetrahydrocurcumin has a hepatoprotective effect against use with erythromycin estolate (broad spectrum antibiotic) as well as with the use of analgesics. Tetrahydrocurcumin has also been shown to have protective properties against nephrotoxicity providing protection of oxidative damage to renal tissue. Tetrahydrocurcumin can also have protection after use with antimalarial drugs, for example chloroquine. Lipid peroxidation caused by disease can also be treated by the anti-oxidative effects of tetrahydrocurcumin.

Liver injury or disease can include but is not limited to alcoholic liver disease, cancer, cirrhosis, cysts, fatty liver disease, fibrosis, hepatitis, jaundice, schlerosing cholangitis, toxic hepatitis, side effects stemming from drug use and acetaminophen toxicity. Liver diseases are a collection of conditions and disorders that can affect the cells of the liver, the liver structure, the liver tissue and can damage or stop liver functions. In some cases liver injury can be caused by a side effect of prolonged medication use. In some embodiments, a method of treating, inhibiting, or ameliorating a disorder in a subject is provided. In some embodiments, the disorder is a liver injury. In some embodiments, the disorder is a liver disease. In some embodiments, the disorder is a liver injury. In some embodiments, the disorder is a fatty liver disease. In some embodiments, the disorder is alcoholic liver disease.

In some embodiments, methods are provided for protecting an organ. In some embodiments, the method comprises identifying a subject in need of protection of an organ and administering the pharmaceutical formulation according to any of embodiments described herein to a subject in need. In some embodiments, the pharmaceutical formulation comprises non-deuterated forms of tetrahydrocurcumin. In some embodiments, the pharmaceutical formulation comprises deuterated forms of tetrahydrocurcumin, as described in several embodiments herein. In some embodiments, the pharmaceutical formulation comprises non-deuterated forms of tetrahydrocurcumin and deuterated forms of tetrahydrocurcumin. In some embodiment, the organ is liver. In some embodiments, the subject suffers from a liver disorder. In some embodiments, the subject suffers from fatty liver disease. In some embodiments, the subject suffers from alcoholic liver disease. In some embodiments, the subject is human. In some embodiments, the administering is performed by oral administration.

In some embodiments, the organ is kidney. In some embodiments, the subject has a kidney disease. In some embodiments, the subject has diabetic kidney disease. In some embodiments, the subject has polycystic kidney disease. In some embodiments, the subject has hypertension. In some embodiments, the subject has hypertension with left ventricular hypertrophy. In some embodiments, the subject is human. In some embodiments, the administering is performed by oral administration.

In some embodiments, the organ is heart. In some embodiments, the subject has heart failure. In some embodiments, the subject has heart disease.

Fibrosis, as described herein, can refer to the formation of excess fibrous connective tissue in an organ or a tissue that can arise from injury. Fibrosis is a process that can be similar to scarring which can include the process of stimulated cells to produce connective tissue, collagen and glycosaminoglycans. Fibrosis can occur in the lungs, liver, heart, soft tissue of the mediastinum, bone marrow, soft tissue of the retroperitoneum, skin, and intestine. In some embodiments, methods are provided for treating, inhibiting, or ameliorating a disorder in a subject. In some embodiments, the subject is suffering from fibrosis.

Kidneys are organs that play a regulatory role in vertebrate organisms. They function by filtering waste products in the blood, regulating blood pressure, electrolyte balance and regulate the red blood cell production in the body. Lack of kidney function can lead to toxicity, a buildup of waste products that can cause weakness, lethargy and confusion. The inability to remove toxins and potassium from the bloodstream can lead to abnormal heart rhythms and sudden death.

Kidney damage that can lead to kidney failure can be caused by many factors. Nephropathy (kidney disease), and Nephritis (inflammatory kidney disease) can be caused by, for example, the use of long term analgesics, a decreased function of xanthine oxidase, polycystic disease of the kidneys, chemotherapy agents, and autoimmune diseases. Kidney disease can include but is not limited to diabetic kidney disease, and polycystic kidney disease. In some embodiments, a method of treating, inhibiting, or ameliorating a disorder in a subject is provided. In some embodiments, the disorder is a kidney disease. In some embodiments, the disorder is diabetic kidney disease. In some embodiments, the disorder is polycystic kidney disease. In some embodiments, methods are provided for protecting an organ. In some embodiment, the organ is kidney.

"Heart failure" can also be referred to as chronic heart failure, and is the inability of the heart to pump sufficiently to maintain the blood flow to meet the body's needs. Causes of heart failure can include but it is not limited to coronary artery disease, a previous myocardial infarction, myocardial infarction (heart attack), high blood pressure, atrial fibrillation, valvular heart disease, excess alcohol use, infection, and cardiomyopathy. In some embodiments of the treatments provided herein, the subject has heart failure. In some embodiments the subject has coronary artery disease, a previous myocardial infarction, myocardial infarction (heart attack), high blood pressure, atrial fibrillation, valvular heart disease, excess alcohol use, infection or a cardiomyopathy. Several embodiments herein relate to the treatment and prevention of heart failure.

Additional Embodiments

The following examples are intended to illustrate, but not to limit, the invention in any manner, shape, or form, either explicitly or implicitly. While they are typical of those that might be used, other procedures, methodologies, or techniques known to those skilled in the art may alternatively be used.

Diagnosis of Liver Damage

In order to determine a subject in need experiments are performed to examine damage by conducting analysis to quantitate levels of Aspartate transaminase (AST) and Alanine transaminase, alkaline phosphatase (ALP), and bilirubin in a subject.

Effect of Pharmaceutical Formulations Comprising Both Tetrahydrocurcumin and Curcumin.

In order to test the effects of tetrahydrocurcumin alone, curcumin alone, and curcumin in combination with tetrahydrocurcumin, diabetic rats and control rats were given oral administration of pharmaceutical formulations comprising of tetrahydrocurcumin alone, curcumin alone, and curcumin in combination with tetrahydrocurcumin. Oral administration of tetrahydrocurcumin was given at 80 mg/kg body weight to 12 diabetic rats and 12 control rats for 45 days. Oral administration of curcumin was given at 100 mg/kg body weight to 12 diabetic rats and 12 control rats for 45 days. Additionally oral administration of a combination of tetrahydrocurcumin (80 mg/kg body weight) and curcumin (100 mg/kg body weight) were given to 12 diabetic rats and 12 control rats for 45 days. After 45 days, the levels of blood glucose, total protein, albumin, globulin and albumin/globulin ratios were examined.

Deuterated Tetrahydrocurcumin for Treatment.

In order to examine the efficacy of tetrahydrocurcumin in the deuterated form, oral administration of deuterated tetrahydrocurcumin was orally administered to 12 diabetic rats and 12 control rats for 45 days (40 mg/kg body weight). Additionally oral administration of deuterated tetrahydrocurcumin was orally administered to 12 diabetic rats and 12 control rats for 45 days with an increased amount of tetrahydrocurcumin (80 mg/kg body weight) As a control, non-deuterated form of tetrahydrocurcumin was orally administered to 12 diabetic rats and 12 control rats for 45 days (40 mg/kg body weight) and non-deuterated form of tetrahydrocurcumin was orally administered to 12 diabetic rats and 12 control rats with an increased concentration of non-deuterated tetrahydrocurcumin (80 mg/kg body weight. In order to examine the efficacy of the drug, the different amounts of the tetrahydrocurcumin were tested in order to examine the effects of the drug concentration to test the ability of the deuterated tetrahydrocurcumin to remain within the system. After 45 days, the levels of blood glucose, total protein, albumin, globulin and albumin/globulin ratios were examined.

mg/dL). BUN was significantly lower in the CKD/THC group at termination of the study, by about 40% compared to the non-treated CKD group. Proteinuria was significantly decreased by almost 50% in CKD/THC compared to non-treated CKD animals. The CKD/THC group showed significant amelioration of hypertension, and a trend for decreased cardiac hypertrophy as measured by normalized heart weight (P=0.06). Image quantitative analysis of Trichrome stained slides of kidney tissue showed a trend for decreased renal fibrosis in CKD/THC animals (P=0.1). Plasma C-reactive protein was not different between CKD groups (P=0.9), suggesting that non-anti-inflammatory mechanisms were at play.

TABLE 1

Table 1: Summary of Results of blood tests following induced CDK.

| Measured parameter | CTL (n = 5) | CKD (n = 6) | CKD/THC (n = 6) | P value comparing CKD groups |
|---|---|---|---|---|
| Systolic blood pressure (mmHg) | 100.2 ± 6.7 | 140 ± 6.4 | 116.5 ± 11.1 | <0.01 |
| Diastolic blood pressure (mmHg) | 79.6 ± 7.7 | 93.7 ± 9.3 | 75.8 ± 12.8 | <0.05 |
| Body weight at termination (g) | 280 ± 19.1 | 259.8 ± 12.9 | 256.8 ± 7.2 | 0.6 |
| Heart wet weight normalized to body weight (g/kg) | 3.54 ± 0.3 | 4.61 ± 0.5 | 3.89 ± 0.61 | 0.06 |
| BUN at termination (mg/dL) | 19.4 ± 2 | 87.1 ± 32.9 | 52.1 ± 19.1 | <0.05 |
| Plasma creatinine (mg/dL) | 0.46 ± 0.15 | 1.37 ± 0.47 | 1.04 ± 0.22 | 0.2 |
| Plasma C-reactive protein (mg/ml) | 1.55 ± 0.81 | 2.77 ± 1.2 | 2.71 ± 0.5 | 0.9 |
| Urine protein/creatinine (mg/g) | 2.15 ± 2.34 | 88.53 ± 30.94 | 47.91 ± 15.42 | <0.05 |
| Kidney fibrosis from Trichrome stained slides: relative % area | 1 ± 0.17 | 1.37 ± 0.03 | 1.16 ± 0.24 | 0.1 |

Dietary Tetrahydrocurcumin Supplementation Slows Progression of Kidney Disease and Decreases Proteinuria in 5/6 Nephrectomy Rats.

Curcumin, a diarylheptanoid present in turmeric, has shown promise as an antioxidant and anti-inflammatory agent in animal models of kidney failure. However, as curcumin is composed of several phenols and some of these compounds may exert paradoxical pro-inflammatory effects, the major metabolite of curcumin, tetrahydrocurcumin (THC) was examined in rats with chronic kidney disease (CKD) for THC effects.

For induction of CKD via nephron mass reduction, Sprague-Dawley rats underwent partial left nephrectomy followed by total right nephrectomy one week later. CKD rats were then randomized to 1% THC diet with polyenylphosphatidylcholine (PPC, 3 g/1000 kcal) vs. regular chow. THC has poor bioavailability, and co-administration with a lipid carrier such as PPC has previously been shown to increase plasma levels 5-fold. Tail blood pressure measurement and 24-hour urine collection were done within a week of study termination. After 9 weeks on special diet, blood and kidneys were collected for biochemical and histologic analyses.

The experimental groups included healthy controls, CTL n=5, non-treated CKD, n=6 and CKD/THC n=6. Findings are summarized in Table 1. At time of randomization to regular chow vs. THC diet, average blood urea nitrogen (BUN) was similar between the CKD groups (63.5+10.5 vs. 66+16.5

As indicated by the experiments, a 1% tetrahydrocurcumin diet decreased the rate of CKD progression in 5/6 nephrectomy rats. There was also a finding that there was significant decrease in proteinuria and hypertension, and a trend for decreased renal fibrosis.

Tetrahydrocurcumin Treatment in Rats.

Rats were induced to have chronic kidney disease via nephron mass reduction, Sprague-Dawley rats underwent partial left nephrectomy followed by total right nephrectomy one week later. CKD rats were then randomized to 1% THC diet with polyenylphosphatidylcholine (PPC, 3 g/1000 kcal) vs. regular chow. The rats were then administered a dose of Buprenex, a narcotic, that can cause kidney damage. As shown in Table 2, are the weights of the test rats during the surgical procedure, before and after the administration of Buprenex.

After 24 hours the rats were analyzed for proteinuria, Galectin-3, and C-reactive protein. Galectin-3 is a marker for cardiac fibrosis, and C-reactive protein is correlated with inflammation. Furthermore, a blood urea nitrogen test (BUN) was carried out with a creatinine and creatinine clearance blood test to evaluate the kidney functions and to look for nephrotoxicity. As shown in Table 3, are the results of the blood tests on the rats following the induced kidney disease.

TABLE 2

Weights of rats following nephrectomy and treatment with Buprenex

| Surgery #2 Right total nephrectomy | | | | | Weights checked week (g) | | |
| --- | --- | --- | --- | --- | --- | --- | --- |
| Date | Wt (g) | Buprenex mL | Doses of Buprenex | Post-op day #1 | Notes | Jan. 28, 2015 | Feb. 12, 2015 |
| Jan. 20, 2015 | 239 | 0.2 | | | | 229 | |
| | 248 | 0.2 | All 8 rats received 2 doses: start of surgery and at 4 pm | # 2 A little scruffy | | 233 | |
| | 228 | 0.2 | | | | 225 | |
| | 234 | 0.2 | | No Buprenex given to any rat | #5: No right kidney found --> Feb. 3, 2015 rat euthanized, R kidney had adhesions to liver | 220 | |
| | 241 | 0.2 | | | | 243 | Rats 1-16 (except 5 and 13) |
| | 250 | 0.2 | | | | 236 | randomized to CKD treatment groups |
| | 251 | 0.2 | | | | 254 | |
| | 235 | 0.2 | | | | 231 Jan. 28, 2015 | |
| Jan. 22, 2015 | 236 | 0.2 | | | | 228 | |
| | 251 | 0.2 | | | | 240 | |
| | 243 | 0.2 | | | | 235 | |
| | 240 | 0.2 | 2 doses Buprenex Dose at start of surgery and at 4 pm | No additional Buprenex to any rats | | 230 | |
| | 238 | 0.2 | | | 1st incision from surgery #1 re-stapled; resulted in some bleeding | 230 | |
| | 248 | 0.2 | | | Rats 14-16 kept in separate cages because #14 and #16 with less well-healed 1st incisions | 238 | |
| | 240 | 0.2 | | | | 237 | |
| Feb. 3, 2015 | 257 | 0.2 | | | | 236 | |
| | 270 | 0.25 | | | | 255 | |
| | 255 | 0.2 | | | | 251 | |
| | 243 | 0.2 | All 8 rats received 2 doses: start of surgery and at 4 pm | | | 243 | |
| | 245 | 0.2 | | | | 243 | Rats randomize to special diets Feb. 12, 2015 |
| | 254 | 0.2 | | | | 267 | |

TABLE 2-continued

Weights of rats following nephrectomy and treatment with Buprenex

| Surgery #2 Right total nephrectomy | | | | | Weights checked week (g) | |
|---|---|---|---|---|---|---|
| Date | Wt (g) | Buprenex mL | Doses of Buprenex | Post-op day #1 | Notes | Jan. 28, 2015 | Feb. 12, 2015 |
| | 224 | 0.2 | | | | | 230 |
| | 248 | 0.2 | | | | | 240 |
| Feb. 5, 2015 | 250 | 0.2 | | | | | 240 |
| | 236 | 0.2 | | | | | 227 |
| | 246 | 0.2 | | | | | 240 |
| | 275 | 0.25 | | | | | 270 |
| | 256 | 0.2 | | | | | 250 |
| | 258 | 0.2 | | | | | 250 |
| | 266 | 0.2 | | | | | 256 |
| | 223 | 0.15 | | | | | 188 |

TABLE 3

Blood test results of rats following induced kidney disease.

| Rat# | 24 hr total proteinuria (mg) | Uprot/Cr ratio mg/g | Cardiac puncture | Terminal BUN mg/dL | Terminal Cr mg/dL | CrCL ml/min*kg | Galectin-3 ng/ml | CRP mg/ml |
|---|---|---|---|---|---|---|---|---|
| 9 | 561.8 | 88.04 | | 73.8 | 0.92 | 2.01 | 694.64 | 4.06 |
| 15 | 655.1 | 52.30 | | 49.8 | 0.96 | 3.30 | 483.86 | 2.77 |
| 20 | 605.8 | 58.89 | | 51.4 | 0.98 | 2.74 | 322.44 | 2.92 |
| 23 | 307.1 | 102.54 | | 117.2 | 1.82 | 0.44 | 380.11 | 3.55 |
| 25 | 1066.0 | 137.39 | | 121.4 | 1.64 | 1.22 | 644.10 | 0.56 |
| 31 | 782.6 | 92.01 | | 109.1 | 1.92 | 1.23 | 326.41 | 2.78 |
| 32 | | | | | | | | |
| 8 | 638.5 | 63.18 | | 44.9 | 0.76 | 3.71 | 285.96 | 2.53 |
| 10 | | | | | | | | |
| 11 | 612.7 | 64.86 | | 60.3 | 1.28 | 1.90 | 450.48 | 3.22 |
| 12 | 355.6 | 30.56 | | 80.6 | 1.25 | 2.56 | 436.37 | 2.15 |
| 14 | 537.7 | 46.32 | | 107.7 | 1.48 | 2.27 | 768.79 | 4.38 |
| 18 | — | — | | 69.9 | 1.19 | — | 273.14 | 2.70 |
| 19 | 613.8 | 43.50 | hemolyzed | 32.1 | 1.13 | 3.46 | — | 3.43 |
| 21 | 410.1 | 37.43 | hemolyzed | 32.6 | 1.01 | 2.91 | — | 2.36 |
| 22 | — | — | | 201.8 | 2.30 | — | 182.38 | 1.19 |
| 27 | — | — | hemolyzed | 62.3 | 0.81 | — | — | 2.57 |
| 1 | 690.5 | 70.69 | | 102.2 | 1.29 | 1.96 | 363.12 | 3.73 |
| 2 | 616.2 | 93.95 | hemolyzed | 90.3 | 1.37 | 1.38 | — | 1.24 |
| 7 | — | — | | 74.7 | 0.93 | — | 277.39 | 1.92 |
| 16 | 844.1 | 81.25 | | 69.4 | 1.38 | 2.20 | 322.99 | 2.70 |
| 17 | — | — | | 50.4 | 1.09 | — | 563.52 | 1.98 |
| 24 | 244.0 | 27.81 | | 30.4 | 0.82 | 2.91 | 707.01 | 2.26 |
| 26 | 817.1 | 108.13 | hemolyzed | 97.8 | 1.12 | 2.00 | — | 0.89 |
| 28 | 710.1 | 68.29 | hemolyzed | 75.7 | 1.11 | 2.49 | — | 0.79 |
| 29 | — | — | | 42.2 | 1.08 | — | 338.09 | 3.85 |
| 30 | — | — | | 36.2 | 1.22 | — | 130.20 | 3.75 |
| 33 | 19.1 | 1.66 | | 19.4 | 0.43 | 6.05 | 244.33 | 2.93 |
| 34 | 6.5 | 0.67 | | 22.4 | 0.71 | 3.25 | 290.48 | 0.97 |
| 35 | 266.2 | 28.31 | | 26.5 | 0.42 | 5.39 | 498.79 | 3.67 |
| 36 | 9.4 | 1.05 | | 17.8 | 0.44 | 5.23 | 632.34 | 1.17 |
| 37 | 8.5 | 1.08 | | 19.8 | 0.31 | 6.66 | 520.15 | 1.65 |
| 38 | 46.8 | 6.28 | | 17.4 | 0.42 | 4.67 | 480.68 | 1.05 |

After inducing chronic kidney disease, the rats were then treated with a pharmaceutical formulation comprising tetrahydrocurcumin, or with a pharmaceutical formulation that had both tetrahydrocurcumin and curcumin. The control group consisted of five rats, (rat numbers 33-38), the rats with CKD (rat number 4, 15, 20, 23, 25, 31), rats with chronic kidney disease treated with tetrahydrocurcumin (rat number 8, 11, 12, 14, 19, 21, 18 and 27) and rats treated with a combination of tetrahydrocurcumin and curcumin (rat number 1, 2, 16, 24, 28, 7, 17, 29 and 30). The results of the change in their blood tests are shown in Tables 4-11. The measurements for the average BUN, blood pressure, body weight, delta BUN, Hgb, and Heart weight/body weight for the four groups are shown in FIGS. 2A-2G. The blood pressures were also measured for the groups of rats, and the study indicated a positive impact of tetrahydrocurcumin on hypertension, as well as development of cardiac hypertrophy.

The blood urea nitrogen test (BUN) is primarily used with the creatinine test to evaluate kidney function and to help diagnose kidney disease. As shown in FIG. 2, panel A and B, there is a decrease in the blood urea nitrogen following treatment with either tetrahydrocurcumin alone or with curcumin (groups 3 and 4), in comparison to the rats with induced kidney disease (group 2). Furthermore, the blood pressure decreased in the treated rats in comparison to the rats with induced kidney disease (group 2) (FIG. 2 panel F and panel G). Therefore the pharmaceutical formulations comprising tetrahydrocurcumin with or without curcumin can be used to treat hypertension. Accordingly, there was no noticeable change in body weight, hemoglobin levels, and heart weight/body weight ratios as seen in FIG. 2 panels C, D and E.

TABLE 4

Change in BUN and heart/body weight following treatment with pharmaceutical formulations comprising tetrahydrocurcumin or both tetrahydrocurcumin and curcumin.

| Group | Rat# | Randomization BUN mg/dL | Terminal BUN mg/dL | Change in BUN | Termination body weight (g) | Term Hgb g/dL | Heart wt (g) | Heart wt/body wt (g/kg) |
|---|---|---|---|---|---|---|---|---|
| 1: CTL | 33 | | 19.4 | | 308 | 13.8 | 1.070 | 3.47 |
| | 34 | | 22.4 | | 290 | 13.8 | 0.977 | 3.37 |
| #35 out | 36 | | 17.8 | | 275 | 14.6 | 0.875 | 3.18 |
| | 37 | | 19.8 | | 265 | 14.1 | 0.995 | 3.75 |
| | 38 | | 17.4 | | 262 | 13.6 | 1.028 | 3.92 |
| | AVE | | 19.4 | | 280 | 13.98 | 0.989 | 3.54 |
| | S.D. | | 2.0 | | 19.1 | 0.4 | 0.073 | 0.30 |
| 2: CKD | 4 | 69.5 | 73.8 | 4.3 | 240 | 14.5 | 0.956 | 3.98 |
| | 15 | 51.9 | 49.8 | -2.1 | 274 | 13 | 1.207 | 4.41 |
| | 20 | 63.7 | 51.4 | -12.3 | 266 | 14.7 | 1.185 | 4.45 |
| | 23 | 50.2 | 117.2 | 67.0 | 259 | 13.1 | 1.219 | 4.71 |
| | 25 | 76.7 | 121.4 | 44.7 | 270 | 14.8 | 1.243 | 4.60 |
| | 31 | 68.7 | 109.1 | 40.4 | 250 | 12.3 | 1.377 | 5.51 |
| | AVE | 63.5 | 87.1 | 23.7 | 259.8 | 13.7 | 1.198 | 4.61 |
| | S.D. | 10.5 | 32.9 | 31.4 | 12.9 | 1.1 | 0.137 | 0.50 |
| 3: CKD/THC | 8 | 58.5 | 44.9 | -13.6 | 250 | 12.7 | 1.169 | 4.68 |
| | 11 | 66.5 | 60.3 | -6.2 | 269 | 13.7 | 0.972 | 3.61 |
| #22 out | 12 | 96.5 | 80.6 | -15.9 | 254 | 13 | 1.165 | 4.59 |
| | 14 | 76.1 | 107.7 | 31.6 | 239 | 11.4 | 1.035 | 4.33 |
| | 19 | 60.8 | 32.1 | -28.7 | 250 | 13.1 | 0.854 | 3.42 |
| | 21 | 47.3 | 32.6 | -14.7 | 258 | 12 | 0.830 | 3.22 |
| | 18 | 66.5 | 69.9 | 3.4 | 272 | 14 | 1.530 | 5.63 |
| | 27 | 66.6 | 62.3 | -4.3 | 260 | 11.8 | 0.989 | 3.80 |
| | AVE | 67.4 | 61.3 | -6.0 | 256.5 | 12.7 | 1.068 | 4.16 |
| | S.D. | 14.4 | 25.5 | 17.9 | 10.7 | 0.9 | 0.224 | 0.80 |
| 4: CKD/THC/ | 1 | 63.3 | 102.2 | 38.9 | 268 | 14.6 | 1.057 | 3.94 |
| curcumin | 2 | 59.5 | 90.3 | 30.8 | 240 | 13.6 | 0.899 | 3.75 |
| | 16 | 95.4 | 69.4 | -26.0 | 238 | 14 | 0.785 | 3.30 |
| #26 out | 24 | 60.9 | 30.4 | -30.5 | 254 | 12.3 | 0.985 | 3.88 |
| | 28 | 52 | 75.7 | 23.7 | 261 | 12.7 | 1.075 | 4.12 |
| | 7 | 80.7 | 74.7 | -6.0 | 265 | 12.9 | 1.029 | 3.88 |
| | 17 | 72.3 | 50.4 | -21.9 | 250 | 13.7 | 1.135 | 4.54 |
| | 29 | 63.7 | 42.2 | -21.5 | 279 | 13.8 | 1.057 | 3.79 |
| | 30 | 64.4 | 36.2 | -28.2 | 266 | 13.5 | 1.016 | 3.82 |
| | AVE | 68.0 | 63.5 | 4.5 | 257.9 | 13.5 | 1.004 | 3.89 |
| | S.D. | 13.1 | 25.0 | 27.9 | 13.5 | 0.7 | 0.105 | 0.33 |
| | ANOVA P < 0.05 between CKD gps | | no | | no | no | no | yes for 2, 4 |

TABLE 5

Measurements of C reactive protein, proteinuria, and Urine protein/creatinine following treatments for chronic kidney disease.

| Group | Rat# | Systolic tail BP mmHg | Diastolic tail BP | Terminal sCr mg/dL | 24 hr total proteinuria (mg) | Uprot/RP mg/ml |
|---|---|---|---|---|---|---|
| 1: CTL | 33 | 97 | 74 | 0.43 | 19.15 | 2.93 |
| | 34 | 99 | 74 | 0.71 | 6.45 | 0.97 |
| #35 out | 36 | 101 | 82 | 0.44 | 9.43 | 1.17 |
| | 37 | 93 | 76 | 0.31 | 8.45 | 1.65 |
| | 38 | 111 | 92 | 0.42 | 46.75 | 1.05 |
| | AVE | 100.2 | 79.6 | 0.46 | 18.05 | 1.55 |
| | S.D. | 6.7 | 7.7 | 0.15 | 16.78 | 0.81 |
| 2: CKD | 4 | 146 | 98 | 0.92 | 561.77 | 4.06 |
| | 15 | 139 | 108 | 0.96 | 655.08 | 2.77 |
| | 20 | 132 | 81 | 0.98 | 605.77 | 2.92 |
| | 23 | 141 | 95 | 1.82 | 307.10 | 3.55 |
| | 25 | 148 | 87 | 1.64 | 1065.96 | 0.56 |
| | 31 | 134 | 93 | 1.92 | 782.57 | 2.78 |

TABLE 5-continued

Measurements of C reactive protein, proteinuria, and Urine protein/creatinine following treatments for chronic kidney disease.

| Group | Rat# | Systolic tail BP mmHg | Diastolic tail BP | Terminal sCr mg/dL | 24 hr total proteinuria (mg) | Uprot/RP mg/ml |
|---|---|---|---|---|---|---|
| | AVE | 140 | 93.7 | 1.37 | 663.04 | 2.77 |
| | S.D. | 6.4 | 9.3 | 0.47 | 251.76 | 1.20 |
| 3: CKD/THC | 8 | 132 | 95 | 0.76 | 638.50 | 2.53 |
| | 11 | 103 | 69 | 1.28 | 612.75 | 3.22 |
| #22 out | 12 | 124 | 60 | 1.25 | 355.61 | 2.15 |
| | 14 | 116 | 78 | 1.48 | 537.69 | 4.38 |
| | 19 | 113 | 81 | 1.13 | 613.82 | 3.43 |
| | 21 | 106 | 67 | 1.01 | 410.08 | 2.36 |
| | 18 | 124 | 77 | 1.19 | | 2.70 |
| | 27 | 121 | 83 | 0.81 | | 2.57 |
| | AVE | 117.4 | 76.3 | 1.11 | 528.07 | 2.92 |
| | S.D. | 9.8 | 10.9 | 0.24 | 118.72 | 0.73 |
| 4: CKD/THC/ | 1 | 121 | 92 | 1.29 | 690.51 | 3.73 |
| curcumin | 2 | 114 | 88 | 1.37 | 616.18 | 1.24 |
| | 16 | 112 | 90 | 1.38 | 844.12 | 2.70 |
| #26 out | 24 | 97 | 57 | 0.82 | 244.03 | 2.26 |
| | 28 | 125 | 84 | 1.11 | 710.12 | 0.79 |
| | 7 | 109 | 81 | 0.93 | | 1.92 |
| | 17 | 107 | 81 | 1.09 | | 1.98 |
| | 29 | 101 | 79 | 1.08 | | 3.85 |
| | 30 | 96 | 74 | 1.22 | | 3.75 |
| | AVE | 109.1 | 80.7 | 1.14 | 620.99 | 2.15 |
| | S.D. | 10.1 | 10.5 | 0.19 | 226.21 | 1.17 |
| | ANOVA P < 0.05 between CKD gps | yes | yes for 2, 3 | | | |

TABLE 6

Table 6: Measurements of Terminal Cr, CrCL (Creatinine Clearance), CRP (C reactive protein) and Galectin-3 following treatments for chronic kidney disease in rats.

| Group | Rat# | Terminal Cr mg/dL | CrCL ml/min * kg | Galectin-3 ng/ml | CRP mg/ml |
|---|---|---|---|---|---|
| 1: CTL | 33 | 0.43 | 6.05 | 244.33 | 2.93 |
| | 34 | 0.71 | 3.25 | 290.48 | 0.97 |
| #35 out | 36 | 0.44 | 5.23 | 632.34 | 1.17 |
| | 37 | 0.31 | 6.66 | 520.15 | 1.65 |
| | 38 | 0.42 | 4.67 | 480.68 | 1.05 |
| | AVE | 0.46 | 5.17 | 433.60 | 1.55 |
| | S.D. | 0.15 | 1.32 | 162.41 | 0.81 |
| 2: CKD | 4 | 0.92 | 2.01 | 694.64 | 4.06 |
| | 15 | 0.96 | 3.30 | 483.86 | 2.77 |
| | 20 | 0.98 | 2.74 | 322.44 | 2.92 |
| | 23 | 1.82 | 0.44 | 380.11 | 3.55 |
| | 25 | 1.64 | 1.22 | 644.10 | 0.56 |
| | 31 | 1.92 | 1.23 | 326.41 | 2.78 |
| | AVE | 1.37 | 1.82 | 475.26 | 2.77 |
| | S.D. | 0.47 | 1.07 | 162.03 | 1.20 |
| 3: CKD/THC | 8 | 0.76 | 3.71 | 285.96 | 2.53 |
| | 11 | 1.28 | 1.90 | 450.48 | 3.22 |
| #22 out | 12 | 1.25 | 2.56 | 436.37 | 2.15 |
| | 14 | 1.48 | 2.27 | 768.79 | 4.38 |
| | 19 | 1.13 | 3.46 | | 3.43 |
| | 21 | 1.01 | 2.91 | | 2.36 |
| | 18 | 1.19 | | 273.14 | 2.70 |
| | 27 | 0.81 | | | 2.57 |
| | AVE | 1.11 | 2.80 | 442.95 | 2.92 |
| | S.D. | 0.24 | 0.70 | 199.84 | 0.73 |
| 4: CKD/THC/ | 1 | 1.29 | 1.96 | 363.12 | 3.73 |
| curcumin | 2 | 1.37 | 1.38 | — | 1.24 |
| | 16 | 1.38 | 2.20 | 322.99 | 2.70 |
| #26 out | 24 | 0.82 | 2.91 | 707.01 | 2.26 |
| | 28 | 1.11 | 2.49 | — | 0.79 |
| | 7 | 0.93 | | 277.39 | 1.92 |
| | 17 | 1.09 | | 563.52 | 1.98 |
| | 29 | 1.08 | | 338.09 | 3.85 |
| | 30 | 1.22 | | 130.20 | 3.75 |
| | AVE | 1.20 | 2.19 | 464.37 | 2.15 |
| | S.D. | 0.23 | 0.57 | 211.08 | 1.17 |
| | ANOVA P < 0.05 between CKD gps | | | | |

TABLE 7

Table 7: Terminal Bun and Terminal Cr measurements in control rats, rats with induced chronic kidney disease (CKD), rats treated with tetrahydrocurcumin after CDK, and rats treated with tetrahydrocurcumin/curcumin after CDK.

| | Rat# | Terminal BUN mg/dL | Terminal Cr mg/dL |
|---|---|---|---|
| Gp 1 CTL | 33 | 19.4 | 0.4 |
| | 34 | 22.4 | 0.7 |
| | 35 | 26.5 | 0.4 |
| | 36 | 17.8 | 0.4 |
| | 37 | 19.8 | 0.3 |
| | 38 | 17.4 | 0.4 |

TABLE 7-continued

Table 7: Terminal Bun and Terminal Cr measurements in control rats, rats with induced chronic kidney disease (CKD), rats treated with tetrahydrocurcumin after CDK, and rats treated with tetrahydrocurcumin/curcumin after CDK.

|  | Rat# | Terminal BUN mg/dL | Terminal Cr mg/dL |
|---|---|---|---|
| Gp 2 CKD | 4 | 73.8 | 0.9 |
|  | 15 | 49.8 | 1.0 |
|  | 20 | 51.4 | 1.0 |
|  | 23 | 117.2 | 1.8 |
|  | 25 | 121.4 | 1.6 |
|  | 31 | 109.1 | 1.9 |
| Gp 3 CKD/thc | 8 | 44.9 | 0.8 |
|  | 11 | 60.3 | 1.3 |
|  | 12 | 80.6 | 1.2 |
|  | 14 | 107.7 | 1.5 |
|  | 18 | 69.9 | 1.2 |
|  | 19 | 32.1 | 1.1 |
|  | 21 | 32.6 | 1.0 |
|  | 22 | 201.8 | 2.3 |
|  | 27 | 62.3 | 0.8 |
| Gp 4 thc/curcumin | 1 | 102.2 | 1.3 |
|  | 2 | 90.3 | 1.4 |
|  | 7 | 74.7 | 0.9 |
|  | 16 | 69.4 | 1.4 |
|  | 17 | 50.4 | 1.1 |
|  | 24 | 30.4 | 0.8 |
|  | 26 | 97.8 | 1.1 |
|  | 28 | 75.7 | 1.1 |
|  | 29 | 42.2 | 1.1 |
|  | 30 | 36.2 | 1.2 |

TABLE 8

Four groups of rats were subjected to blood tests to examine changes in BUN weight and Hgb following treatment with tetrahydrocurcumin or a combination of tetrahydrocurcumin with curcumin. The groups were control, rats with induced CKD, rats treated with tetrahydrocurcumin following induced CKD, and rats treated with tetrahydrocurcumin/curcumin following induced CKD.

| Rat# | Randomization BUN mg/dL | Terminal BUN mg/dL | Change in BUN | Termination body weight (g) | Term Hgb g/dL | Heart wt (g) | Heart wt/body wt (g/kg) |
|---|---|---|---|---|---|---|---|
| 33 |  | 19.4 |  | 308 | 13.8 | 1.070 | 3.47 |
| 34 |  | 22.4 |  | 290 | 13.8 | 0.977 | 3.37 |
| 36 |  | 17.8 |  | 275 | 14.6 | 0.875 | 3.18 |
| 37 |  | 19.8 |  | 265 | 14.1 | 0.995 | 3.75 |
| 38 |  | 17.4 |  | 262 | 13.6 | 1.028 | 3.92 |
| AVE |  | 19.4 |  | 280 | 13.98 | 0.989 | 3.54 |
| S.D. |  | 2.0 |  | 19.1 | 0.4 | 0.073 | 0.30 |
| 4 | 69.5 | 73.8 | 4.3 | 240 | 14.5 | 0.956 | 3.98 |
| 15 | 51.9 | 49.8 | −2.1 | 274 | 13 | 1.207 | 4.41 |
| 20 | 63.7 | 51.4 | −12.3 | 266 | 14.7 | 1.185 | 4.45 |
| 23 | 50.2 | 117.2 | 67.0 | 259 | 13.1 | 1.219 | 4.71 |
| 25 | 76.7 | 121.4 | 44.7 | 270 | 14.8 | 1.243 | 4.60 |
| 31 | 68.7 | 109.1 | 40.4 | 250 | 12.3 | 1.377 | 5.51 |
| AVE | 63.5 | 87.1 | 23.7 | 259.8 | 13.7 | 1.198 | 4.61 |
| S.D. | 10.5 | 32.9 | 31.4 | 12.9 | 1.1 | 0.137 | 0.50 |
| 8 | 58.5 | 44.9 | −13.6 | 250 | 12.7 | 1.169 | 4.68 |
| 11 | 66.5 | 60.3 | −6.2 | 269 | 13.7 | 0.972 | 3.61 |
| 12 | 96.5 | 80.6 | −15.9 | 254 | 13 | 1.165 | 4.59 |
| 19 | 60.8 | 32.1 | −28.7 | 250 | 13.1 | 0.854 | 3.42 |
| 21 | 47.3 | 32.6 | −14.7 | 258 | 12 | 0.830 | 3.22 |
| 27 | 66.6 | 62.3 | −4.3 | 260 | 11.8 | 0.989 | 3.80 |
| AVE | 66.0 | 52.1 | −13.9 | 256.8 | 12.7 | 0.997 | 3.89 |
| S.D. | 16.5 | 19.1 | 8.7 | 7.2 | 0.7 | 0.146 | 0.61 |
| ANOVA P < 0.05? |  | Y | Y |  |  |  | Y |
| P-value Gp 1&2 |  | <0.01 |  |  | n.s. |  | <0.01 |
| P-value Gp 2&3 |  | <0.05 | ttest <0.05 |  | n.s. |  | n.s. 0.06 |
| P-value Gp 1&3 |  | n.s. | <0.05 |  | <0.05 |  | n.s. 0.5 |

TABLE 9

Three groups of rats were subjected to blood tests to examine changes in uprot/CR, CrCL, Galectin-3 and CRP measurements following treatment with tetrahydrocurcumin or a combination of tetrahydrocurcumin with curcumin. The groups were control, rats with induced CKD, and rats treated with tetrahydrocurcumin/curcumin following induced CKD.

| Group | Rat# | Diastolic tail BP | Terminal sCr mg/dL | 24 hr total proteinuria (mg) | Uprot/Cr ratio mg/g | CrCL ml/min*kg | Galectin-3 ng/ml | CRP mg/ml |
|---|---|---|---|---|---|---|---|---|
| 1: CTL | 33 | 74 | 0.43 | 19.15 | 1.66 | 6.05 | 244.33 | 2.93 |
|  | 34 | 74 | 0.71 | 6.45 | 0.67 | 3.25 | 290.48 | 0.97 |
| #35 out | 36 | 82 | 0.44 | 9.43 | 1.05 | 5.23 | 632.34 | 1.17 |
|  | 37 | 76 | 0.31 | 8.45 | 1.08 | 6.66 | 520.15 | 1.65 |
|  | 38 | 92 | 0.42 | 46.75 | 6.28 | 4.67 | 480.68 | 1.05 |
|  | AVE | 79.6 | 0.46 | 18.05 | 2.15 | 5.17 | 433.60 | 1.55 |
|  | S.D. | 7.7 | 0.15 | 16.78 | 2.34 | 1.32 | 162.41 | 0.81 |
| 2: CKD | 4 | 98 | 0.92 | 561.77 | 88.04 | 2.01 | 694.64 | 4.06 |
|  | 15 | 108 | 0.96 | 655.08 | 52.30 | 3.30 | 483.86 | 2.77 |
|  | 20 | 81 | 0.98 | 605.77 | 58.89 | 2.74 | 322.44 | 2.92 |
|  | 23 | 95 | 1.82 | 307.10 | 102.54 | 0.44 | 380.11 | 3.55 |
|  | 25 | 87 | 1.64 | 1065.96 | 137.39 | 1.22 | 644.10 | 0.56 |
|  | 31 | 93 | 1.92 | 782.57 | 92.01 | 1.23 | 326.41 | 2.78 |
|  | AVE | 93.7 | 1.37 | 663.04 | 88.53 | 1.82 | 475.26 | 2.77 |
|  | S.D. | 9.3 | 0.47 | 251.76 | 30.94 | 1.07 | 162.03 | 1.20 |
| 3: CKD/THC | 8 | 95 | 0.76 | 638.50 | 63.18 | 3.71 | 285.96 | 2.53 |
|  | 11 | 69 | 1.28 | 612.75 | 64.86 | 1.90 | 450.48 | 3.22 |
| #14, 18, 22 out | 12 | 60 | 1.25 | 355.61 | 30.56 | 2.56 | 436.37 | 2.15 |
|  | 19 | 81 | 1.13 | 613.82 | 43.50 | 3.46 | hemolyzed | 3.43 |
|  | 21 | 67 | 1.01 | 410.08 | 37.43 | 2.91 | hemolyzed | 2.36 |
|  | 27 | 83 | 0.81 |  |  |  | hemolyzed | 2.57 |
|  | AVE | 75.8 | 1.04 | 526.15 | 47.91 | 2.91 | 390.94 | 2.71 |
|  | S.D. | 12.8 | 0.22 | 132.63 | 15.42 | 0.72 | 91.19 | 0.50 |
|  | ANOVA P < 0.05? | Y | Y | Y | Y | Y |  | P = 0.07 |
| Tukey posthoc test | P-value Gp 1&2 | n.s. | <0.01 | <0.01 | <0.01 | <0.01 |  | 0.09 |
|  | P-value Gp 2&3 | <0.05 | n.s. 0.2 | n.s. | n.s. | <0.05 | n.s. | 0.9 |
|  | P-value Gp 1&3 | n.s. | <0.05 | <0.01 | <0.05 | <0.05 |  | 0.12 |

TABLE 10

Table 10: The three groups of rats of Table 7 were then killed and examined for fibrosis of the kidney. The table presents the relative percent area of fibrosis in the kidneys of the three groups. The groups were control, rats with induced CKD, and rats treated with tetrahydrocurcumin/curcumin following induced CKD.

| Kidney slides Trichrome stain | Relative % area fibrosis | | |
|---|---|---|---|
| Gp 1 CTL | 0.809435 | | |
|  | 1.182758 | Ave | 1 |
|  | 1.050894 | SD | 0.1674 |
|  | 1.197113 | | |
|  | 0.886911 | | |
|  | 0.872889 | | |
| Gp 2 CKD | 1.382136 | | |
|  | 1.374501 | Ave | 1.3719 |
|  | 1.422038 | SD | 0.0315 |
|  | 1.337959 | | |
|  | 1.337959 | | |
|  | 1.376647 | | |
| Gp 3 CKD/THC | 1.395675 | | |
|  | 1.32091 | Ave | 1.1551 |
|  | 1.345161 | SD | 0.2435 |
|  | 0.895843 | | |
|  | 1.146017 | | |
|  | 0.826866 | | |

TABLE 11

Table 11: Measurement of nephrosis in the kidneys of the four groups of rats (Control, induced CKD, treatment of tetrahydrocurcumin following induced CKD and treatment of tetrahydrocurcumin/curcumin following induced CKD).

| | | | % area |
|---|---|---|---|
| Group 1 CTL | | | |
| Sample 1 | | | |
| 1 | 1228794 | 0.164 | 16.409 |
| 2 | 1228793 | 0.23 | 23.042 |
| 3 | 1228796 | 0.13 | 12.971 |
|  |  | average | 17.474 |
| Sample 2 | | | |
| 1 | 1228798 | 0.296 | 29.641 |
| 2 | 1228797 | 0.424 | 42.357 |
| 3 | 1228796 | 0.282 | 28.157 |
|  |  | average | 33.385 |
| Sample 3 | | | |
| 1 | 1228742 | 0.655 | 65.538 |
| 2 | 1228792 | 0.275 | 27.505 |
| 3 | 1228794 | 0.247 | 24.726 |
|  |  | average | 39.25633 |
| Sample 4 | | | |
| 1 | 1228798 | 0.201 | 20.091 |
| 2 | 1228800 | 0.156 | 15.635 |
| 3 | 1228800 | 0.193 | 19.348 |
|  |  | Average | 18.358 |

The results of the treatment of the rats show a positive impact of THC on hypertension, as well as development of cardiac hypertrophy, as seen in the effects for the diastolic and systolic blood pressure following treatment with tetrahydrocurcumin with or without the addition of curcumin (Tables 1, 5 and 9).

TABLE 11-continued

Table 11: Measurement of nephrosis in the kidneys of the four groups of rats (Control, induced CKD, treatment of tetrahydrocurcumin following induced CKD and treatment of tetrahydrocurcumin/curcumin following induced CKD).

|  |  |  | % area |
|---|---|---|---|
| Sample 5 | | | |
| 1 | 1228800 | 0.533 | 53.268 |
| 2 | 1228765 | 0.543 | 54.287 |
| 3 | 1228779 | 0.634 | 63.369 |
| | | Average | 56.97467 |
| Sample 6 | | | |
| 1 | 1228798 | 0.228 | 22.761 |
| 2 | 1228800 | 0.276 | 27.583 |
| 3 | 1228800 | 0.243 | 24.289 |
| | | Average | 24.87767 |
| Group 2 CKD | | | |
| Sample 1 | | | |
| 1 | 1228773 | 0.339 | 33.922 |
| 2 | 1228776 | 0.49 | 48.959 |
| 3 | 1228785 | 0.413 | 41.258 |
| | | average | 41.37967 |
| Sample 2 | | | |
| 1 | 1228798 | 0.521 | 52.065 |
| 2 | 1228711 | 0.548 | 54.831 |
| 3 | 1228715 | 0.684 | 68.382 |
| | | Average | 58.426 |
| Sample 3 | | | |
| 1 | 1228774 | 0.816 | 81.636 |
| 2 | 1228662 | 0.781 | 78.07 |
| 3 | 1228800 | 0.787 | 78.746 |
| | | Average | 79.484 |
| Sample 4 | | | |
| 1 | 1228799 | 0.699 | 69.937 |
| 2 | 1228789 | 0.766 | 76.573 |
| 3 | 1228715 | 0.684 | 68.382 |
| | | Average | 71.63067 |
| Sample 5 | | | |
| 1 | 1228768 | 0.648 | 64.842 |
| 2 | 1228792 | 0.555 | 55.475 |
| 3 | 1228790 | 0.532 | 53.175 |
| | | Average | 57.83067 |
| Sample 6 | | | |
| 1 | 1228780 | 0.758 | 75.769 |
| 2 | 1228789 | 0.725 | 72.53 |
| 3 | 1228798 | 0.754 | 75.45 |
| | | Average | 74.583 |
| Group 3 CKD + THC | | | |
| Sample 1 | | | |
| 1 | 1228765 | 0.719 | 71.895 |
| 2 | 1228757 | 0.714 | 71.431 |
| 3 | 1228757 | 0.737 | 73.721 |
| | | Average | 72.349 |
| Sample 2 | | | |
| 1 | 1228774 | 0.617 | 61.721 |
| 2 | 1228776 | 0.668 | 66.83 |
| 3 | 1228752 | 0.696 | 69.556 |
| | | Average | 66.03567 |
| Sample 3 | | | |
| 1 | 1228792 | 0.79 | 79.041 |
| 2 | 1228766 | 0.601 | 60.075 |
| 3 | 1228788 | 0.695 | 69.458 |
| | | Average | 69.52467 |
| Sample 4 | | | |
| 1 | 1228775 | 0.491 | 49.106 |
| 2 | 1228797 | 0.556 | 55.623 |
| 3 | 1228798 | 0.207 | 20.679 |
| | | Average | 41.80267 |
| Sample 5 | | | |
| 1 | 1228739 | 0.321 | 32.058 |
| 2 | 1228781 | 0.418 | 41.754 |
| 3 | 1228799 | 0.166 | 16.589 |
| | | Average | 30.13367 |
| Sample 6 | | | |
| 1 | 1228791 | 0.399 | 39.869 |
| 2 | 1228791 | 0.177 | 17.667 |
| 3 | 1228799 | 0.365 | 36.541 |
| | | Average | 31.359 |
| Group 4 CKD + THC/curcumin | | | |
| Sample 1 | | | |
| 1 | 1228755 | 0.55 | 55.01 |
| 2 | 1228775 | 0.447 | 44.687 |
| 3 | 1228730 | 0.409 | 40.908 |
| | | Average | 46.86833 |
| Sample 2 | | | |
| 1 | 1228599 | 0.503 | 50.288 |
| 2 | 1228793 | 0.539 | 53.913 |
| 3 | 1228759 | 0.53 | 52.979 |
| | | Average | 52.39333 |
| Sample 3 | | | |
| 1 | 1228770 | 0.667 | 66.679 |
| 2 | 1228772 | 0.557 | 55.669 |
| 3 | 1228747 | 0.49 | 48.983 |
| | | Average | 57.11033 |
| Sample 4 | | | |
| 1 | 1228743 | 0.541 | 54.148 |
| 2 | 1228723 | 0.615 | 61.512 |
| 3 | 1228780 | 0.557 | 55.733 |
| | | Average | 57.131 |
| Sample 5 | | | |
| 1 | 1228729 | 0.685 | 68.474 |
| 2 | 1228799 | 0.502 | 50.178 |
| 3 | 1228745 | 0.637 | 63.737 |
| | | Average | 60.79633 |
| Sample 6 | | | |
| 1 | 1228761 | 0.706 | 70.589 |
| 2 | 1228752 | 0.401 | 40.136 |
| 3 | 1228761 | 0.725 | 72.516 |
| | | Average | 61.08033 |

More Embodiments

In some embodiments, a pharmaceutical formulation is provided. In some embodiments, the pharmaceutical formulation comprises a non-deuterated form of tetrahydrocurcumin and a pharmaceutical vehicle. In some embodiments, the pharmaceutical formulation further comprises a first lipid. In some embodiments, the first lipid is a phospholipid. In some embodiments, the first lipid is polyenylphosphatidylcholine. In some embodiments, the pharmaceutical formulation comprises at least 5% of the first lipid by weight. In some embodiments, the pharmaceutical formulation comprises no more than 95% of the first lipid by weight. In some embodiments, the pharmaceutical formulation further comprises a second lipid. In some embodiments, the pharmaceutical formulation comprises at least 5% of the second lipid by weight. In some embodiments, the pharmaceutical formulation comprises no more than 95% of the second lipid by weight. In some embodiments, the second lipid is omega-3. In some embodiments, the second lipid is omega-3 from fish or flaxseed. In some embodiments, the pharmaceutical formulation further comprises an antioxidant. In some embodiments, the pharmaceutical formulation comprises at least 5% of antioxidant by weight. In some embodiments, the pharmaceutical formulation comprises no more than 95% of the antioxidant by weight. In some embodiments, the antioxidant is Vitamin E. In some embodiments, the antioxidant is Vitamin C. In some embodiments, the antioxidant is alpha lipoic acid. In some embodiments, the pharmaceutical formulation further comprises curcumin. In some embodiments, the pharmaceutical formulation further comprises a terpenoid. In some embodiments, the pharmaceutical formulation further comprises cysteamine. In some embodiments, the pharmaceutical formulation further comprises pantethine. In some embodiments, the curcumin is deuterated. In some embodiments, the vehicle is a lipophilic solvent, fatty oil, organic oil, or liposome. In some embodiments, the pharmaceutical formulation further comprises an excipient. In some embodiments, the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In some embodiments, the pharmaceutical formulation further comprises baicalin.

In some embodiments, a method of treating, inhibiting, or ameliorating a disorder in a subject is provided. In some embodiments, the method comprises administering the pharmaceutical formulation of any of the embodiments described herein to the subject. In some embodiments, the pharmaceutical formulation comprises a non-deuterated form of tetrahydrocurcumin and a pharmaceutical vehicle. In some embodiments, the pharmaceutical formulation further comprises a first lipid. In some embodiments, the first lipid is a phospholipid. In some embodiments, the first lipid is polyenylphosphatidylcholine. In some embodiments, the pharmaceutical formulation comprises at least 5% of the first lipid by weight. In some embodiments, the pharmaceutical formulation comprises no more than 95% of the first lipid by weight. In some embodiments, the pharmaceutical formulation further comprises a second lipid. In some embodiments, the pharmaceutical formulation comprises at least 5% of the second lipid by weight. In some embodiments, the pharmaceutical formulation comprises no more than 95% of the second lipid by weight. In some embodiments, the second lipid is omega-3. In some embodiments, the second lipid is omega-3 from fish or flaxseed. In some embodiments, the pharmaceutical formulation further comprises an antioxidant. In some embodiments, the pharmaceutical formulation comprises at least 5% of antioxidant by weight. In some embodiments, the pharmaceutical formulation comprises no more than 95% of the antioxidant by weight. In some embodiments, the antioxidant is Vitamin E. In some embodiments, the antioxidant is Vitamin C. In some embodiments, the antioxidant is alpha lipoic acid. In some embodiments, the pharmaceutical formulation further comprises curcumin. In some embodiments, the pharmaceutical formulation further comprises a terpenoid. In some embodiments, the pharmaceutical formulation further comprises cysteamine. In some embodiments, the pharmaceutical formulation further comprises pantethine. In some embodiments, the curcumin is deuterated. In some embodiments, the vehicle is a lipophilic solvent, fatty oil, organic oil, or liposome. In some embodiments, the pharmaceutical formulation further comprises an excipient. In some embodiments, the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In some embodiments, the pharmaceutical formulation further comprises baicalin. In some embodiments, the disorder is a liver disorder. In some embodiments, the disorder is a fatty liver disease. In some embodiments, the disorder is alcoholic liver disease. In some embodiments, the disorder is a kidney disease. In some embodiments, the disorder is diabetic kidney disease. In some embodiments, the disorder is polycystic kidney disease. In some embodiments, the disorder is hypertension. In some embodiments, the disorder is hypertension with left ventricular hypertrophy. In some embodiments, the disorder is diabetes. In some embodiments, the disorder is diabetes with hyperlipidemia. In some embodiments, the subject has elevated Galectin-3 levels in the blood and/or urine. In some embodiments, the subject has elevated levels of fibrotic markers. In some embodiments, the fibrotic markers are in blood. In some embodiments, the fibrotic markers are in urine. In some embodiments, the subject has an elevated level of a marker of oxidative stress. In some embodiments, the marker of oxidative stress is in blood. In some embodiments, the marker of oxidative stress is in urine. In some embodiments, the subject has an elevated level of a marker of inflammation. In some embodiments, the marker of inflammation is in blood. In some embodiments, the marker of inflammation is in urine. In some embodiments, the pharmaceutical formulation is administered to the subject by oral administration. In some embodiments, the administering is performed by intravenous administration. In some embodiments, the subject is human. In some embodiments, the subject is taking analgesics. In some embodiments, the subject is under treatment with one or more anti-malarial drugs. In some embodiments, the subject has heart failure.

In some embodiments, a method of protecting an organ is provided. In some embodiments, the method comprises identifying a subject in need of protection of an organ and administering the pharmaceutical formulation of any of the embodiments described herein to a subject in need. In some embodiments, the pharmaceutical formulation comprises a non-deuterated form of tetrahydrocurcumin and a pharmaceutical vehicle. In some embodiments, the pharmaceutical formulation further comprises a first lipid. In some embodiments, the first lipid is a phospholipid. In some embodiments, the first lipid is polyenylphosphatidylcholine. In some embodiments, the pharmaceutical formulation comprises at least 5% of the first lipid by weight. In some embodiments, the pharmaceutical formulation comprises no more than 95% of the first lipid by weight. In some embodiments, the pharmaceutical formulation further comprises a second lipid. In some embodiments, the pharmaceutical formulation comprises at least 5% of the second lipid by weight. In some embodiments, the pharmaceutical formulation comprises no more than 95% of the second lipid by weight. In some embodiments, the second lipid is omega-3. In some embodiments, the second lipid is omega-3 from fish or flaxseed. In some embodiments, the pharmaceutical formulation further comprises an antioxidant. In some embodiments, the pharmaceutical formulation comprises at least 5% of antioxidant by weight. In some embodiments, the pharmaceutical formulation comprises no more than 95% of the antioxidant by weight. In some embodiments, the antioxidant is Vitamin E. In some embodiments, the antioxidant is Vitamin C. In some embodiments, the antioxidant is alpha lipoic acid. In some embodiments, the pharmaceutical formulation further comprises curcumin. In some embodiments, the pharmaceutical formulation further comprises a terpenoid. In some embodiments, the pharmaceutical formulation further comprises cysteamine. In some embodiments, the pharmaceutical formulation further comprises pantethine. In some embodiments, the curcumin is deuterated. In some embodiments, the vehicle is a lipophilic solvent, fatty oil, organic oil, or liposome. In some embodiments, the pharmaceutical formulation further comprises an excipient. In some embodiments, the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In some embodiments, the pharmaceutical formulation further comprises baicalin. In some embodiments, the organ is kidney. In some embodiments, the organ is liver. In some embodiments, the organ is heart. In some embodiments, the subject is human. In some embodiments, the administering is performed by oral administration. In some embodiments, the administering is performed by intravenous administration. In some embodiments, the subject has a liver disorder. In some embodiments, the subject has a fatty liver disease. In some embodiments, the subject has alcoholic liver disease. In some embodiments, the subject has a kidney disease. In some embodiments, the subject has diabetic kidney disease. In some embodiments, the subject has polycystic kidney disease. In some embodiments, the subject has hypertension. In some embodiments, the subject has hypertension with left ventricular hypertrophy. In some embodiments, the subject has diabetes. In some embodiments, the subject has diabetes with hyperlipidemia. In some embodiments, the subject has an elevated level of Galectin-3 in the blood or urine. In some embodiments, the subject has an elevated level of one or more fibrotic markers. In some embodiments, at least one of the one or more fibrotic markers is in blood. In some embodiments, at least one of the one or more fibrotic markers is in urine. In some embodiments, the subject has an elevated level of one or more markers of oxidative stress. In some embodiments, at least one of the markers of oxidative stress is in blood. In some embodiments, at least one of the markers of oxidative stress is in urine. In some embodiments, the subject has an elevated level of one or more markers of inflammation. In some embodiments, at least one of the elevated markers is in urine. In some embodiments, the subject has heart failure.

In some embodiments, a method of preventing heart failure in a subject in need is provided. In some embodiments, the method comprises identifying a subject in need of prevention of heart failure and administering the pharmaceutical formulation of any one of the embodiments described herein to a subject in need. In some embodiments, the pharmaceutical formulation comprises a non-deuterated form of tetrahydrocurcumin and a pharmaceutical vehicle. In some embodiments, the pharmaceutical formulation further comprises a first lipid. In some embodiments, the first lipid is a phospholipid. In some embodiments, the first lipid is polyenylphosphatidylcholine. In some embodiments, the pharmaceutical formulation comprises at least 5% of the first lipid by weight. In some embodiments, the pharmaceutical formulation comprises no more than 95% of the first lipid by weight. In some embodiments, the pharmaceutical formulation further comprises a second lipid. In some embodiments, the pharmaceutical formulation comprises at least 5% of the second lipid by weight. In some embodiments, the pharmaceutical formulation comprises no more than 95% of the second lipid by weight. In some embodiments, the second lipid is omega-3. In some embodiments, the second lipid is omega-3 from fish or flaxseed. In some embodiments, the pharmaceutical formulation further comprises an antioxidant. In some embodiments, the pharmaceutical formulation comprises at least 5% of antioxidant by weight. In some embodiments, the pharmaceutical formulation comprises no more than 95% of the antioxidant by weight. In some embodiments, the antioxidant is Vitamin E. In some embodiments, the antioxidant is Vitamin C. In some embodiments, the antioxidant is alpha lipoic acid. In some embodiments, the pharmaceutical formulation further comprises curcumin. In some embodiments, the pharmaceutical formulation further comprises a terpenoid. In some embodiments, the pharmaceutical formulation further comprises cysteamine. In some embodiments, the pharmaceutical formulation further comprises pantethine. In some embodiments, the curcumin is deuterated. In some embodiments, the vehicle is a lipophilic solvent, fatty oil, organic oil, or liposome. In some embodiments, the pharmaceutical formulation further comprises an excipient. In some embodiments, the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In some embodiments, the pharmaceutical formulation further comprises baicalin. In some embodiments, the subject has chronic kidney disease and/or hypertension. In some embodiments, the subject is human. In some embodiments, the administering is performed by oral administration. In some embodiments, the administering is performed by intravenous administration.

In some embodiments, a deuterated form of tetrahydrocurcumin is provided. In some embodiments, the deuterated form of tetrahydrocurcumin has at least one deuterated site. In some embodiments, the deuterated form of tetrahydrocurcumin has at least five deuterated sites. In some embodiments, the deuterated form of tetrahydrocurcumin has at least ten deuterated sites. In some embodiments, the deuterated form of tetrahydrocurcumin has no more than fifteen deuterated sites. In some embodiments, the deuterated form of tetrahydrocurcumin is deuterated at one or two alcohol sites. In some embodiments, the deuterated form of tetrahydrocurcumin has at least 1 deuteron. In some embodiments, the deuterated form of tetrahydrocurcumin has at least 5 deuterons. In some embodiments, the deuterated form of tetrahydrocurcumin has at least 10 deuterons. In some embodiments, the deuterated form of tetrahydrocurcumin has at least 20 deuterons. In some embodiments, the deuterated form of tetrahydrocurcumin has at least 24 deuterons.

In some embodiments, a deuterated form of tetrahydrocurcumin is provided. In some embodiments, the deuterated form of tetrahydrocurcumin is manufactured by any of the embodiments described herein. In some embodiments, a method of making a deuterated form of tetrahydrocurcumin is provided. In some embodiments, the method comprises contacting tetrahydrocurcumin in the presence of a catalyst and deuterated water under a condition to form the deuterated form of tetrahydrocurcumin. In some embodiments, the method further comprises hydrogenating curcumin to form the tetrahydrocurcumin. In some embodiments, the deuterated form of tetrahydrocurcumin has at least one deuterated site. In some embodiments, the deuterated form of tetrahydrocurcumin has at least five deuterated sites. In some embodiments, the deuterated form of tetrahydrocurcumin has at least ten deuterated sites. In some embodiments, the deuterated form of tetrahydrocurcumin has no more than fifteen deuterated sites. In some embodiments, the deuterated form of tetrahydrocurcumin is deuterated at one or two alcohol sites. In some embodiments, the deuterated form of tetrahydrocurcumin has no more than twenty-four deuterons. In some embodiments, the deuterated form of tetrahydrocurcumin has at least 1 deuteron. In some embodiments, the deuterated form of tetrahydrocurcumin has at least 5 deuterons. In some embodiments, the deuterated form of tetrahydrocurcumin has at least 10 deuterons. In some embodiments, the deuterated form of tetrahydrocurcumin has at least 20 deuterons. In some embodiments, the deuterated form of tetrahydrocurcumin has at least 24 deuterons. In some embodiments, the catalyst is palladium on carbon. In some embodiments, the catalyst is palladium barium carbonate. In some embodiments, the catalyst is palladium barium sulphate. In some embodiments, the catalyst is palladium silica. In some embodiments, the catalyst is palladium alumina. In some embodiments, the catalyst is platinum on carbon. In some embodiments, the catalyst is platinum-palladium carbon. In some embodiments, the catalyst is platinum alumina. In some embodiments, the catalyst is platinum calcium carbonate. In some embodiments, the catalyst is platinum barium sulfate. In some embodiments, the catalyst is platinum silica. In some embodiments, the catalyst is platinum graphite. In some embodiments, the method further comprises purifying the deuterated form of tetrahydrocurcumin. In some embodiments, the purifying step comprises isolating the deuterated form of tetrahydrocurcumin with column chromatography. In some embodiments, the deuterated water is at least 25% deuterated. In some embodiments, the deuterated water is at least 50% deuterated. In some embodiments, the deuterated water is at least 75% deuterated. In some embodiments, the deuterated water is 100% deuterated.

In some embodiments, a pharmaceutical formulation is provided. In some embodiments, the pharmaceutical formulation comprises the tetrahydrocurcumin of any of the embodiments described herein and a pharmaceutical vehicle. In some embodiments, the deuterated form of tetrahydrocurcumin has at least one deuterated site. In some embodiments, the deuterated form of tetrahydrocurcumin has at least five deuterated sites. In some embodiments, the deuterated form of tetrahydrocurcumin has at least ten deuterated sites. In some embodiments, the deuterated form of tetrahydrocurcumin has no more than fifteen deuterated sites. In some embodiments, the deuterated form of tetrahydrocurcumin is deuterated at one or two alcohol sites. In some embodiments, the deuterated form of tetrahydrocurcumin has at least 1 deuteron. In some embodiments, the deuterated form of tetrahydrocurcumin has at least 5 deuterons. In some embodiments, the deuterated form of tetrahydrocurcumin has at least 10 deuterons. In some embodiments, the deuterated form of tetrahydrocurcumin has at least 20 deuterons. In some embodiments, the deuterated form of tetrahydrocurcumin has at least 24 deuterons. In some embodiments, the deuterated form of tetrahydrocurcumin is manufactured by any of the embodiments described herein. In some embodiments, the method comprises contacting tetrahydrocurcumin in the presence of a catalyst and deuterated water under a condition to form the deuterated form of tetrahydrocurcumin. In some embodiments, the method further comprises hydrogenating curcumin to form the tetrahydrocurcumin. In some embodiments, the deuterated form of tetrahydrocurcumin has at least one deuterated site. In some embodiments, the deuterated form of tetrahydrocurcumin has at least five deuterated sites.

In some embodiments, the deuterated form of tetrahydrocurcumin has at least ten deuterated sites. In some embodiments, the deuterated form of tetrahydrocurcumin has no more than fifteen deuterated sites. In some embodiments, the deuterated form of tetrahydrocurcumin is deuterated at one or two alcohol sites. In some embodiments, the deuterated form of tetrahydrocurcumin has no more than twenty-four deuterons. In some embodiments, the deuterated form of tetrahydrocurcumin has at least 1 deuteron. In some embodiments, the deuterated form of tetrahydrocurcumin has at least 5 deuterons. In some embodiments, the deuterated form of tetrahydrocurcumin has at least 10 deuterons. In some embodiments, the deuterated form of tetrahydrocurcumin has at least 20 deuterons. In some embodiments, the deuterated form of tetrahydrocurcumin has at least 24 deuterons. In some embodiments, the catalyst is palladium on carbon. In some embodiments, the catalyst is palladium barium carbonate. In some embodiments, the catalyst is palladium barium sulphate. In some embodiments, the catalyst is palladium silica. In some embodiments, the catalyst is palladium alumina. In some embodiments, the catalyst is platinum on carbon. In some embodiments, the catalyst is platinum-palladium carbon. In some embodiments, the catalyst is platinum alumina. In some embodiments, the catalyst is platinum calcium carbonate. In some embodiments, the catalyst is platinum barium sulfate. In some embodiments, the catalyst is platinum silica. In some embodiments, the catalyst is platinum graphite. In some embodiments, the method further comprises purifying the deuterated form of tetrahydrocurcumin. In some embodiments, the purifying step comprises isolating the deuterated form of tetrahydrocurcumin with column chromatography. In some embodiments, the deuterated water is at least 25% deuterated. In some embodiments, the deuterated water is at least 50% deuterated. In some embodiments, the deuterated water is at least 75% deuterated. In some embodiments, the deuterated water is 100% deuterated. In some embodiments, the pharmaceutical formulation further comprises a first lipid. In some embodiments, the first lipid is a phospholipid. In some embodiments, the first lipid is polyenylphosphatidylcholine. In some embodiments, the pharmaceutical formulation comprises at least 5% of the first lipid by weight. In some embodiments, the pharmaceutical formulation comprises no more than 95% of the first lipid by weight. In some embodiments, the pharmaceutical formulation further comprises a second lipid. In some embodiments, the pharmaceutical formulation comprises at least 5% of the second lipid by weight. In some embodiments, the pharmaceutical formulation comprises no more than 95% of the second lipid by weight. In some embodiments, the second lipid is omega-3. In some embodiments, the second lipid is omega-3 from fish or flaxseed. In some embodiments, the pharmaceutical formulation further comprises an antioxidant. In some embodiments, the pharmaceutical formulation comprises at least 5% of antioxidant by weight. In some embodiments, the pharmaceutical formulation comprises no more than 95% of the antioxidant by weight. In some embodiments, the antioxidant is Vitamin E. In some embodiments, the antioxidant is Vitamin C. In some embodiments, the antioxidant is alpha lipoic acid. In some embodiments, the pharmaceutical formulation further comprises curcumin. In some embodiments, the pharmaceutical formulation further comprises a terpenoid. In some embodiments, the pharmaceutical formulation further comprises cysteamine. In some embodiments, the pharmaceutical formulation further comprises pantethine. In some embodiments, the curcumin is deuterated. In some embodiments, the pharmaceutical formulation further comprises baicalin. In some embodiments, the vehicle is a lipophilic solvent, fatty oil, organic oil, or liposome. In some embodiments, the pharmaceutical formulation further comprises an excipient. In some embodiments, the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

In some embodiments, a method of treating, inhibiting, or ameliorating a disorder in a subject is provided. In some embodiments, the method comprises administering the pharmaceutical formulation of any one of the embodiments described herein to the subject. In some embodiments, the pharmaceutical formulation comprises the tetrahydrocurcumin of any of the embodiments described herein and a pharmaceutical vehicle. In some embodiments, the deuterated form of tetrahydrocurcumin has at least one deuterated site. In some embodiments, the deuterated form of tetrahydrocurcumin has at least five deuterated sites. In some embodiments, the deuterated form of tetrahydrocurcumin has at least ten deuterated sites. In some embodiments, the deuterated form of tetrahydrocurcumin has no more than fifteen deuterated sites. In some embodiments, the deuterated form of tetrahydrocurcumin is deuterated at one or two alcohol sites. In some embodiments, the deuterated form of tetrahydrocurcumin has at least 1 deuteron. In some embodiments, the deuterated form of tetrahydrocurcumin has at least 5 deuterons. In some embodiments, the deuterated form of tetrahydrocurcumin has at least 10 deuterons. In some embodiments, the deuterated form of tetrahydrocurcumin has at least 20 deuterons. In some embodiments, the deuterated form of tetrahydrocurcumin has at least 24 deuterons. In some embodiments, the deuterated form of tetrahydrocurcumin is manufactured by any of the embodiments described herein. In some embodiments, the method comprises contacting tetrahydrocurcumin in the presence of a catalyst and deuterated water under a condition to form the deuterated form of tetrahydrocurcumin. In some embodiments, the method further comprises hydrogenating curcumin to form the tetrahydrocurcumin. In some embodiments, the deuterated form of tetrahydrocurcumin has at least one deuterated site. In some embodiments, the deuterated form of tetrahydrocurcumin has at least five deuterated sites. In some embodiments, the deuterated form of tetrahydrocurcumin has at least ten deuterated sites. In some embodiments, the deuterated form of tetrahydrocurcumin has no more than fifteen deuterated sites. In some embodiments, the deuterated form of tetrahydrocurcumin is deuterated at one or two alcohol sites. In some embodiments, the deuterated form of tetrahydrocurcumin has no more than twenty-four deuterons. In some embodiments, the deuterated form of tetrahydrocurcumin has at least 1 deuteron. In some embodiments, the deuterated form of tetrahydrocurcumin has at least 5 deuterons. In some embodiments, the deuterated form of tetrahydrocurcumin has at least 10 deuterons. In some embodiments, the deuterated form of tetrahydrocurcumin has at least 20 deuterons. In some embodiments, the deuterated form of tetrahydrocurcumin has at least 24 deuterons. In some embodiments, the catalyst is palladium on carbon. In some embodiments, the catalyst is palladium barium carbonate. In some embodiments, the catalyst is palladium barium sulphate. In some embodiments, the catalyst is palladium silica. In some embodiments, the catalyst is palladium alumina. In some embodiments, the catalyst is platinum on carbon. In some embodiments, the catalyst is platinum-palladium carbon. In some embodiments, the catalyst is platinum alumina. In some embodiments, the catalyst is platinum calcium carbonate. In some embodiments, the catalyst is platinum barium sulfate. In some embodiments, the catalyst is platinum silica. In some embodiments, the catalyst is platinum graphite. In some embodiments, the method further comprises purifying the deuterated form of tetrahydrocurcumin. In some embodiments, the purifying step comprises isolating the deuterated form of tetrahydrocurcumin with column chromatography. In some embodiments, the deuterated water is at least 25% deuterated. In some embodiments, the deuterated water is at least 50% deuterated. In some embodiments, the deuterated water is at least 75% deuterated. In some embodiments, the deuterated water is 100% deuterated. In some embodiments, the pharmaceutical formulation further comprises a first lipid. In some embodiments, the first lipid is a phospholipid. In some embodiments, the first lipid is polyenylphosphatidylcholine. In some embodiments, the pharmaceutical formulation comprises at least 5% of the first lipid by weight. In some embodiments, the pharmaceutical formulation comprises no more than 95% of the first lipid by weight. In some embodiments, the pharmaceutical formulation further comprises a second lipid. In some embodiments, the pharmaceutical formulation comprises at least 5% of the second lipid by weight. In some embodiments, the pharmaceutical formulation comprises no more than 95% of the second lipid by weight. In some embodiments, the second lipid is omega-3. In some embodiments, the second lipid is omega-3 from fish or flaxseed. In some embodiments, the pharmaceutical formulation further comprises an antioxidant. In some embodiments, the pharmaceutical formulation comprises at least 5% of antioxidant by weight. In some embodiments, the pharmaceutical formulation comprises no more than 95% of the antioxidant by weight. In some embodiments, the antioxidant is Vitamin E. In some embodiments, the antioxidant is Vitamin C. In some embodiments, the antioxidant is alpha lipoic acid. In some embodiments, the pharmaceutical formulation further comprises curcumin. In some embodiments, the pharmaceutical formulation further comprises a terpenoid. In some embodiments, the pharmaceutical formulation further comprises cysteamine. In some embodiments, the pharmaceutical formulation further comprises pantethine. In some embodiments, the curcumin is deuterated. In some embodiments, the pharmaceutical formulation further comprises baicalin. In some embodiments, the vehicle is a lipophilic solvent, fatty oil, organic oil, or liposome. In some embodiments, the pharmaceutical formulation further comprises an excipient. In some embodiments, the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In some embodiments, the disorder is a liver disorder. In some embodiments, the disorder is a fatty liver disease. In some embodiments, the disorder is alcoholic liver disease. In some embodiments, the disorder is heart failure. In some embodiments, the disorder is a kidney disease. In some embodiments, the disorder is diabetic kidney disease. In some embodiments, the disorder is polycystic kidney disease. In some embodiments, the disorder is hypertension. In some embodiments, the disorder is hypertension with left ventricular hypertrophy. In some embodiments, the disorder is diabetes. In some embodiments, the disorder is diabetes with hyperlipidemia. In some embodiments, the subject has elevated Galectin-3 levels in the blood or urine. In some embodiments, the subject has elevated levels of fibrotic markers. In some embodiments, the fibrotic markers are in blood. In some embodiments, the fibrotic markers are in urine. In some embodiments, the subject has an elevated level of a marker of oxidative stress. In some embodiments, the marker of oxidative stress is in blood. In some embodiments, the marker of oxidative stress is in urine. In some embodiments, the subject has an elevated level of a marker of inflammation. In some embodiments, the marker of inflammation is in blood. In some embodiments, the marker of inflammation is in urine. In some embodiments, the pharmaceutical formulation is administered to the subject by oral administration. In some embodiments, the administering is performed by intravenous administration. In some embodiments, the subject is human. In some embodiments, the subject is taking analgesics. In some embodiments, the subject is under treatment with one or more anti-malarial drugs.

In some embodiments, a method of protecting an organ is provided. In some embodiments, the method comprises identifying a subject in need of protection of an organ and administering the pharmaceutical formulation of any one of the embodiments described herein, to a subject in need. In some embodiments, the pharmaceutical formulation comprises the tetrahydrocurcumin of any of the embodiments described herein and a pharmaceutical vehicle. In some embodiments, the deuterated form of tetrahydrocurcumin has at least one deuterated site. In some embodiments, the deuterated form of tetrahydrocurcumin has at least five deuterated sites. In some embodiments, the deuterated form of tetrahydrocurcumin has at least ten deuterated sites. In some embodiments, the deuterated form of tetrahydrocurcumin has no more than fifteen deuterated sites. In some embodiments, the deuterated form of tetrahydrocurcumin is deuterated at one or two alcohol sites. In some embodiments, the deuterated form of tetrahydrocurcumin has at least 1 deuteron. In some embodiments, the deuterated form of tetrahydrocurcumin has at least 5 deuterons. In some embodiments, the deuterated form of tetrahydrocurcumin has at least 10 deuterons. In some embodiments, the deuterated form of tetrahydrocurcumin has at least 20 deuterons. In some embodiments, the deuterated form of tetrahydrocurcumin has at least 24 deuterons. In some embodiments, the deuterated form of tetrahydrocurcumin is manufactured by any of the embodiments described herein. In some embodiments, the method comprises contacting tetrahydrocurcumin in the presence of a catalyst and deuterated water under a condition to form the deuterated form of tetrahydrocurcumin. In some embodiments, the method further comprises hydrogenating curcumin to form the tetrahydrocurcumin. In some embodiments, the deuterated form of tetrahydrocurcumin has at least one deuterated site. In some embodiments, the deuterated form of tetrahydrocurcumin has at least five deuterated sites. In some embodiments, the deuterated form of tetrahydrocurcumin has at least ten deuterated sites. In some embodiments, the deuterated form of tetrahydrocurcumin has no more than fifteen deuterated sites. In some embodiments, the deuterated form of tetrahydrocurcumin is deuterated at one or two alcohol sites. In some embodiments, the deuterated form of tetrahydrocurcumin has no more than twenty-four deuterons. In some embodiments, the deuterated form of tetrahydrocurcumin has at least 1 deuteron. In some embodiments, the deuterated form of tetrahydrocurcumin has at least 5 deuterons. In some embodiments, the deuterated form of tetrahydrocurcumin has at least 10 deuterons. In some embodiments, the deuterated form of tetrahydrocurcumin has at least 20 deuterons. In some embodiments, the deuterated form of tetrahydrocurcumin has at least 24 deuterons. In some embodiments, the catalyst is palladium on carbon. In some embodiments, the catalyst is palladium barium carbonate. In some embodiments, the catalyst is palladium barium sulphate. In some embodiments, the catalyst is palladium silica. In some embodiments, the catalyst is palladium alumina. In some embodiments, the catalyst is platinum on carbon. In some embodiments, the catalyst is platinum-palladium carbon. In some embodiments, the catalyst is platinum alumina. In some embodiments, the catalyst is platinum calcium carbonate. In some embodiments, the catalyst is platinum barium sulfate. In some embodiments, the catalyst is platinum silica. In some embodiments, the catalyst is platinum graphite. In some embodiments, the method further comprises purifying the deuterated form of tetrahydrocurcumin. In some embodiments, the purifying step comprises isolating the deuterated form of tetrahydrocurcumin with column chromatography. In some embodiments, the deuterated water is at least 25% deuterated. In some embodiments, the deuterated water is at least 50% deuterated. In some embodiments, the deuterated water is at least 75% deuterated. In some embodiments, the deuterated water is 100% deuterated. In some embodiments, the pharmaceutical formulation further comprises a first lipid. In some embodiments, the first lipid is a phospholipid. In some embodiments, the first lipid is polyenylphosphatidylcholine. In some embodiments, the pharmaceutical formulation comprises at least 5% of the first lipid by weight. In some embodiments, the pharmaceutical formulation comprises no more than 95% of the first lipid by weight. In some embodiments, the pharmaceutical formulation further comprises a second lipid. In some embodiments, the pharmaceutical formulation comprises at least 5% of the second lipid by weight. In some embodiments, the pharmaceutical formulation comprises no more than 95% of the second lipid by weight. In some embodiments, the second lipid is omega-3. In some embodiments, the second lipid is omega-3 from fish or flaxseed. In some embodiments, the pharmaceutical formulation further comprises an antioxidant. In some embodiments, the pharmaceutical formulation comprises at least 5% of antioxidant by weight. In some embodiments, the pharmaceutical formulation comprises no more than 95% of the antioxidant by weight. In some embodiments, the antioxidant is Vitamin E. In some embodiments, the antioxidant is Vitamin C. In some embodiments, the antioxidant is alpha lipoic acid. In some embodiments, the pharmaceutical formulation further comprises curcumin. In some embodiments, the pharmaceutical formulation further comprises a terpenoid. In some embodiments, the pharmaceutical formulation further comprises cysteamine. In some embodiments, the pharmaceutical formulation further comprises pantethine. In some embodiments, the curcumin is deuterated. In some embodiments, the pharmaceutical formulation further comprises baicalin. In some embodiments, the vehicle is a lipophilic solvent, fatty oil, organic oil, or liposome. In some embodiments, the pharmaceutical formulation further comprises an excipient. In some embodiments, the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In some embodiments, the organ is kidney. In some embodiments, the organ is liver. In some embodiments, the organ is heart. In some embodiments, the subject is human. In some embodiments, the administering is performed by oral administration. In some embodiments, the administering is performed by intravenous administration. In some embodiments, the subject is human. In some embodiments, the subject has a liver disorder. In some embodiments, the subject has a fatty liver disease. In some embodiments, the subject has alcoholic liver disease. In some embodiments, the subject has a kidney disease. In some embodiments, the subject has diabetic kidney disease. In some embodiments, the subject has polycystic kidney disease. In some embodiments, the subject has hypertension. In some embodiments, the subject has hypertension with left ventricular hypertrophy. In some embodiments, the subject has diabetes. In some embodiments, the subject has diabetes with hyperlipidemia. In some embodiments, the subject has an elevated level of Galectin-3 in the blood or urine. In some embodiments, the subject has an elevated level of one or more fibrotic markers. In some embodiments, at least one of the one or more fibrotic markers is in blood. In some embodiments, at least one of the one or more fibrotic markers is in urine. In some embodiments, the subject has an elevated level of one or more markers of oxidative stress. In some embodiments, at least one of the markers of oxidative stress is in blood. In some embodiments, at least one of the markers of oxidative stress is in urine. In some embodiments, at least one of the elevated markers of inflammation is in blood. In some embodiments, the subject has an elevated level of one or more markers of inflammation. In some embodiments, at least one of the elevated markers of inflammation is in blood. In some embodiments, at least one of the elevated markers is in urine. In some embodiments, the subject has heart failure.

In some embodiments, a method of treating or preventing heart failure in a subject in need is provided. In some embodiments, the method comprises identifying a subject in need of treatment for or prevention of heart failure and administering the pharmaceutical formulation of any of the embodiments described herein to a subject in need. In some embodiments, the pharmaceutical formulation comprises the tetrahydrocurcumin of any of the embodiments described herein and a pharmaceutical vehicle. In some embodiments, the deuterated form of tetrahydrocurcumin has at least one deuterated site. In some embodiments, the deuterated form of tetrahydrocurcumin has at least five deuterated sites. In some embodiments, the deuterated form of tetrahydrocurcumin has at least ten deuterated sites. In some embodiments, the deuterated form of tetrahydrocurcumin has no more than fifteen deuterated sites. In some embodiments, the deuterated form of tetrahydrocurcumin is deuterated at one or two alcohol sites. In some embodiments, the deuterated form of tetrahydrocurcumin has at least 1 deuteron. In some embodiments, the deuterated form of tetrahydrocurcumin has at least 5 deuterons. In some embodiments, the deuterated form of tetrahydrocurcumin has at least 10 deuterons. In some embodiments, the deuterated form of tetrahydrocurcumin has at least 20 deuterons. In some embodiments, the deuterated form of tetrahydrocurcumin has at least 24 deuterons. In some embodiments, the deuterated form of tetrahydrocurcumin is manufactured by any of the embodiments described herein. In some embodiments, the method comprises contacting tetrahydrocurcumin in the presence of a catalyst and deuterated water under a condition to form the deuterated form of tetrahydrocurcumin. In some embodiments, the method further comprises hydrogenating curcumin to form the tetrahydrocurcumin. In some embodiments, the deuterated form of tetrahydrocurcumin has at least one deuterated site. In some embodiments, the deuterated form of tetrahydrocurcumin has at least five deuterated sites. In some embodiments, the deuterated form of tetrahydrocurcumin has at least ten deuterated sites. In some embodiments, the deuterated form of tetrahydrocurcumin has no more than fifteen deuterated sites. In some embodiments, the deuterated form of tetrahydrocurcumin is deuterated at one or two alcohol sites. In some embodiments, the deuterated form of tetrahydrocurcumin has no more than twenty-four deuterons. In some embodiments, the deuterated form of tetrahydrocurcumin has at least 1 deuteron. In some embodiments, the deuterated form of tetrahydrocurcumin has at least 5 deuterons. In some embodiments, the deuterated form of tetrahydrocurcumin has at least 10 deuterons. In some embodiments, the deuterated form of tetrahydrocurcumin has at least 20 deuterons. In some embodiments, the deuterated form of tetrahydrocurcumin has at least 24 deuterons. In some embodiments, the catalyst is palladium on carbon. In some embodiments, the catalyst is palladium barium carbonate. In some embodiments, the catalyst is palladium barium sulphate. In some embodiments, the catalyst is palladium silica. In some embodiments, the catalyst is palladium alumina. In some embodiments, the catalyst is platinum on carbon. In some embodiments, the catalyst is platinum-palladium carbon. In some embodiments, the catalyst is platinum alumina. In some embodiments, the catalyst is platinum calcium carbonate. In some embodiments, the catalyst is platinum barium sulfate. In some embodiments, the catalyst is platinum silica. In some embodiments, the catalyst is platinum graphite. In some embodiments, the method further comprises purifying the deuterated form of tetrahydrocurcumin. In some embodiments, the purifying step comprises isolating the deuterated form of tetrahydrocurcumin with column chromatography. In some embodiments, the deuterated water is at least 25% deuterated. In some embodiments, the deuterated water is at least 50% deuterated. In some embodiments, the deuterated water is at least 75% deuterated. In some embodiments, the deuterated water is 100% deuterated. In some embodiments, the pharmaceutical formulation further comprises a first lipid. In some embodiments, the first lipid is a phospholipid. In some embodiments, the first lipid is polyenylphosphatidylcholine. In some embodiments, the pharmaceutical formulation comprises at least 5% of the first lipid by weight. In some embodiments, the pharmaceutical formulation comprises no more than 95% of the first lipid by weight. In some embodiments, the pharmaceutical formulation further comprises a second lipid. In some embodiments, the pharmaceutical formulation comprises at least 5% of the second lipid by weight. In some embodiments, the pharmaceutical formulation comprises no more than 95% of the second lipid by weight. In some embodiments, the second lipid is omega-3. In some embodiments, the second lipid is omega-3 from fish or flaxseed. In some embodiments, the pharmaceutical formulation further comprises an antioxidant. In some embodiments, the pharmaceutical formulation comprises at least 5% of antioxidant by weight. In some embodiments, the pharmaceutical formulation comprises no more than 95% of the antioxidant by weight. In some embodiments, the antioxidant is Vitamin E. In some embodiments, the antioxidant is Vitamin C. In some embodiments, the antioxidant is alpha lipoic acid. In some embodiments, the pharmaceutical formulation further comprises curcumin. In some embodiments, the pharmaceutical formulation further comprises a terpenoid. In some embodiments, the pharmaceutical formulation further comprises cysteamine. In some embodiments, the pharmaceutical formulation further comprises pantethine. In some embodiments, the curcumin is deuterated. In some embodiments, the pharmaceutical formulation further comprises baicalin. In some embodiments, the vehicle is a lipophilic solvent, fatty oil, organic oil, or liposome. In some embodiments, the pharmaceutical formulation further comprises an excipient. In some embodiments, the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In some embodiments, the subject has chronic kidney disease and/or hypertension. In some embodiments, the subject is human. In some embodiments, the administering is performed by oral administration. In some embodiments, the administering is performed by intravenous administration.

In one aspect a method of manufacturing tetrahydrocurcumin from curcumin is contemplated. In some embodiments, the tetrahydrocurcumin is deuterated.

In another aspect, tetrahydrocurcumin is manufactured synthetically. In some embodiments, curcumin is not a substrate in the manufacturing of tetrahydrocurcumin. In some embodiments, the tetrahydrocurcumin is deuterated.

In some embodiments, a pharmaceutical formulation, for example a pharmaceutical formulation, comprising a non-deuterated form of tetrahydrocurcumin is provided. In some embodiments, the pharmaceutical formulation further comprises a pharmaceutical vehicle. In some embodiments, the pharmaceutical formulation can further comprise a deuterated form of tetrahydrocurcumin and a pharmaceutical vehicle. In some embodiments, the deuterated form of tetrahydrocurcumin has no more than fifteen deuterated sites. In some embodiments, the deuterated form of tetrahydrocurcumin has at least ten deuterated sites. In some embodiments, the deuterated form of tetrahydrocurcumin has at least five deuterated sites. In some embodiments, the deuterated form of tetrahydrocurcumin has at least one deuterated site. In some embodiments, the deuterated form of tetrahydrocurcumin is deuterated at one or two alcohol sites. In some embodiments, the deuterated form of tetrahydrocurcumin has at least 1 deuteron. In some embodiments, the deuterated form of tetrahydrocurcumin has at least 5 deuterons. In some embodiments, the deuterated form of tetrahydrocurcumin has at least 10 deuterons. In some embodiments, the deuterated form of tetrahydrocurcumin has at least 20 deuterons. In some embodiments, the deuterated form of tetrahydrocurcumin has at least 24 deuterons.

In some embodiments, the pharmaceutical formulation further comprises a first lipid. In some embodiments, the first lipid is a phospholipid. In some embodiments, the first lipid is polyenylphosphatidylcholine. In some embodiments, the pharmaceutical formulation comprises at least 5% of the first lipid by weight. In some embodiments, the pharmaceutical formulation comprises no more than 95% of the first lipid by weight. In some embodiments, the pharmaceutical formulation comprises a second lipid. In some embodiments, the pharmaceutical formulation comprises at least 5% of the second lipid by weight. In some embodiments, the pharmaceutical formulation comprises no more than 95% of the second lipid by weight. In some embodiments, the second lipid is omega-3. In some embodiments, the second lipid is omega-3 from fish or flaxseed.

In some embodiments, the pharmaceutical formulation comprises an antioxidant. In some embodiments, the pharmaceutical formulation comprises at least 5% of antioxidant by weight. In some embodiments, the pharmaceutical formulation comprises no more than 95% of the antioxidant by weight. In some embodiments, the antioxidant is Vitamin E. In some embodiments, the antioxidant is Vitamin C. In some embodiments, the antioxidant is alpha lipoic acid.

In some embodiments, the pharmaceutical formulation further comprises curcumin. In some embodiments, the curcumin is deuterated. In some embodiments, the pharmaceutical formulation comprises a terpenoid. In some embodiments, the pharmaceutical formulation comprises cysteamine. In some embodiments, the pharmaceutical formulation comprises pantethine. In some embodiments, the pharmaceutical formulation comprises baicalin.

In some embodiments, a method of treating, inhibiting, or ameliorating a disorder in a subject is provided. In some embodiments, the method comprises administering a pharmaceutical formulation according to any of the embodiments described herein to the subject. In some embodiments, the pharmaceutical formulation comprises a non-deuterated form of tetrahydrocurcumin. In some embodiments, the pharmaceutical formulation comprises a deuterated form of tetrahydrocurcumin. In some embodiments, the pharmaceutical formulation comprises a non-deuterated form of tetrahydrocurcumin and a deuterated form of tetrahydrocurcumin. In some embodiments, the disorder is a liver disorder. In some embodiments, the disorder is a fatty liver disease. In some embodiments, the disorder is alcoholic liver disease. In some embodiments, the disorder is a kidney disease. In some embodiments, the disorder is diabetic kidney disease. In some embodiments, the disorder is polycystic kidney disease. In some embodiments, the disorder is heart failure.

In some embodiments, the pharmaceutical formulation is administered to treat, prevent or ameliorate a disease. In some embodiments, the disease is hypertension or cardiac hypertrophy.

In some embodiments, the pharmaceutical formulation is administered to treat a subject suffering from heart failure. In some embodiments, the pharmaceutical formulation is administered to a subject to prevent heart failure. In some embodiments, the subject suffers from hypertension. In some embodiments, the subject suffers from chronic kidney disease.

In some embodiments, the disorder is hypertension. In some embodiments, the disorder is hypertension with left ventricular hypertrophy. In some embodiments, the disorder is diabetes. In some embodiments, the disorder is diabetes with hyperlipidemia. In some embodiments, the disorder is cardiac hypertrophy.

In some embodiments, the subject has elevated Galectin-3 levels in the blood. In some embodiments, the subject has elevated levels of fibrotic markers. In some embodiments, the fibrotic markers are in blood. In some embodiments, the fibrotic markers are in urine. In some embodiments, the subject has an elevated level of a marker of oxidative stress. In some embodiments, the marker of oxidative stress is in blood. In some embodiments, the marker of oxidative stress is in urine. In some embodiments, the subject has an elevated level of a marker of inflammation. In some embodiments, the marker of inflammation is in blood. In some embodiments, the marker of inflammation is in urine.

In some embodiments, the pharmaceutical formulation is administered to the subject by oral administration. In some embodiments, the pharmaceutical formulation comprises a non-deuterated form of tetrahydrocurcumin. In some embodiments, the pharmaceutical formulation comprises a deuterated form of tetrahydrocurcumin. In some embodiments, the pharmaceutical formulation comprises a non-deuterated form of tetrahydrocurcumin and a deuterated form of tetrahydrocurcumin. In some embodiments, the subject is human. In some embodiments, the administering is performed by intravenous administration. In some embodiments, the subject is under treatment with one or more antimalarial drugs.

In some embodiments, a method of protecting an organ is provided. In some embodiments, the method comprises identifying a subject in need of protection of an organ and administering the pharmaceutical formulation according to any of the embodiments described herein to the subject in need. In some embodiments, the pharmaceutical formulation comprises a non-deuterated form of tetrahydrocurcumin. In some embodiments, the pharmaceutical formulation comprises a deuterated form of tetrahydrocurcumin. In some embodiments, the pharmaceutical formulation comprises a non-deuterated form of tetrahydrocurcumin and a deuterated form of tetrahydrocurcumin. In some embodiments, the organ is kidney. In some embodiments, the organ is liver. In some embodiments, the subject is human. In some embodiments, the organ is heart.

In some embodiments, the administering is performed by oral administration. In some embodiments, the administering is performed by intravenous administration. In some embodiments, the subject has a liver disorder. In some embodiments, the subject has a fatty liver disease. In some embodiments, the subject has alcoholic liver disease. In some embodiments, the subject has a kidney disease. In some embodiments, the subject has diabetic kidney disease. In some embodiments, the subject has polycystic kidney disease. In some embodiments, the subject has heart failure.

In some embodiments, the subject has hypertension. In some embodiments, the subject has hypertension with left ventricular hypertrophy. In some embodiments, the subject has diabetes. In some embodiments, the subject has diabetes with hyperlipidemia.

In some embodiments, the subject has an elevated level of Galectin-3 in the blood. In some embodiments, the subject has an elevated level of one or more fibrotic markers. In some embodiments, the one or more fibrotic markers are in blood. In some embodiments, at least one of the one or more fibrotic markers is in urine. In some embodiments, the subject has an elevated level of one or more markers of oxidative stress. In some embodiments, at least one of the markers of oxidative stress is in blood. In some embodiments, at least one of the markers of oxidative stress is in urine. In some embodiments, the subject has an elevated level of one or more markers of inflammation. In some embodiments, at least one of the elevated markers of inflammation is in blood. In some embodiments, at least one of the elevated markers is in urine.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

What is claimed is:

1. A method of treating, inhibiting, or ameliorating a disorder in a subject, the method comprising:
    identifying a subject having a disorder selected from the group consisting of alcoholic liver disease, hypertension with left ventricular hypertrophy, and cardiac hypertrophy; and
    administering a pharmaceutical formulation to the subject, the pharmaceutical formulation comprising a non-deuterated form of tetrahydrocurcumin or a deuterated form of tetrahydrocurcumin and a pharmaceutical vehicle.

2. The method of claim 1, wherein the subject has elevated levels of Galectin-3, fibrotic markers, markers of oxidative stress, and/or markers of inflammation in the blood and/or urine, or wherein the subject is taking analgesics, or wherein the subject is under treatment with one or more anti-malarial drugs.

3. The method of claim 1, wherein the pharmaceutical formulation is administered by oral administration.

4. A method of protecting an organ, comprising:
    identifying a subject in need of protection of an organ, the organ selected from kidney, liver and heart; and
    administering a pharmaceutical formulation to a subject in need thereof, the pharmaceutical formulation comprising a deuterated form of tetrahydrocurcumin at greater than natural isotopic abundance and a pharmaceutical vehicle.

5. The method of claim 4, wherein the administering is performed by oral administration.

6. The method of claim 4, wherein the subject has a disorder selected from a group consisting liver disorder, fatty liver disease, alcoholic liver disease, kidney disease, chronic kidney disease, diabetic kidney disease, polycystic kidney disease, hypertension, hypertension with left ventricular hypertrophy, diabetes, diabetes with hyperlipidemia and heart failure.

7. The method of claim 3, wherein the subject has an elevated level of Galectin-3, fibrotic markers, markers of oxidative stress and/or one or more markers of inflammation in the blood and/or urine.

8. A method of treating or preventing heart failure in a subject in need, comprising:
identifying a subject in need of treatment for or prevention of heart failure; and
administering pharmaceutical formulation to a subject in need thereof, the pharmaceutical formulation comprising a deuterated form of tetrahydrocurcumin at greater than natural isotopic abundance and a pharmaceutical vehicle.

9. The method of claim 8, wherein the subject has chronic kidney disease and/or hypertension.

10. The method of claim 8, wherein the administering is oral administration.

11. A pharmaceutical formulation comprising a deuterated form of tetrahydrocurcumin at greater than natural isotopic abundance and a pharmaceutical vehicle.

12. The pharmaceutical formulation of claim 11, further comprising a first lipid, wherein the first lipid is a phospholipid or polyenylphosphatidylcholine, and wherein the pharmaceutical formulation comprises at least 5% of the first lipid by weight and no more than 95% of the first lipid by weight.

13. The pharmaceutical formulation of claim 11, further comprising a second lipid, and wherein the pharmaceutical formulation comprises at least 5% of the second lipid by weight and no more than 95% of the second lipid by weight.

14. The pharmaceutical formulation of claim 11, wherein the pharmaceutical formulation further comprises an antioxidant, and wherein the pharmaceutical formulation comprises at least 5% of antioxidant by weight and no more than 95% of the antioxidant by weight, and wherein the antioxidant is selected from a group consisting of Vitamin E, Vitamin C and alpha lipoic acid.

15. The pharmaceutical formulation of claim 11, wherein the pharmaceutical formulation further comprises curcumin, a terpenoid, cysteamine, pantethine, and/or baicalin.

16. The pharmaceutical formulation of claim 11, wherein the vehicle is a lipophilic solvent, fatty oil, organic oil, or liposome.

17. The pharmaceutical formulation of claim 11, wherein the pharmaceutical formulation further comprises an excipient, wherein the excipient is a sugar, lactose, sucrose, mannitol, sorbitol, cellulose preparations of maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP).

18. The method of claim 1, wherein the pharmaceutical formulation is administered by intravenous administration.

19. The method of claim 1, wherein the pharmaceutical formulation is administered by parenteral administration.

20. The method of claim 19, wherein the parenteral administration is subcutaneous.

21. The method of claim 19, wherein the parenteral administration is inhalational.

22. The method of claim 19, wherein the parenteral administration is selected from the group consisting of intramuscular, intramedullary, intrathecal, direct intraventricular, intranasal, intraocular, colonical, rectal, vaginal, nasal, and intraperitoneal.

23. The method of claim 4, wherein the administering is performed by intravenous administration.

24. The method of claim 4, wherein the administering is performed by parenteral administration.

25. The method of claim 24, wherein the parenteral administration is subcutaneous.

26. The method of claim 24, wherein the parenteral administration is inhalational.

27. The method of claim 24, wherein the parenteral administration is selected from the group consisting of intramuscular, intramedullary, intrathecal, direct intraventricular, intranasal, intraocular, colonical, rectal, vaginal, nasal, and intraperitoneal.

28. The method of claim 8, wherein the administering is intravenous administration.

29. The method of claim 8, wherein the administering is parenteral administration.

30. The method of claim 29, wherein the parenteral administration is subcutaneous.

31. The method of claim 29, wherein the parenteral administration is inhalational.

32. The method of claim 29, wherein the parenteral administration is selected from the group consisting of intramuscular, intramedullary, intrathecal, direct intraventricular, intranasal, intraocular, colonical, rectal, vaginal, nasal, and intraperitoneal.

\* \* \* \* \*